United States Patent
Berzofsky et al.

(10) Patent No.: US 9,421,254 B2
(45) Date of Patent: Aug. 23, 2016

(54) IMMUNOSTIMULATORY COMBINATIONS OF TLR LIGANDS AND METHODS OF USE

(75) Inventors: Jay A. Berzofsky, Bethesda, MD (US); Qing Zhu, Bethesda, MD (US); Igor Belyakov, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 348 days.

(21) Appl. No.: 12/679,881

(22) PCT Filed: Sep. 24, 2008

(86) PCT No.: PCT/US2008/011236
§ 371 (c)(1),
(2), (4) Date: Aug. 11, 2010

(87) PCT Pub. No.: WO2009/088401
PCT Pub. Date: Jul. 16, 2009

(65) Prior Publication Data
US 2010/0297165 A1 Nov. 25, 2010

Related U.S. Application Data

(60) Provisional application No. 60/995,212, filed on Sep. 24, 2007.

(51) Int. Cl.
*A61K 39/00* (2006.01)
*A61K 39/38* (2006.01)
*A61K 45/00* (2006.01)
*A61K 51/00* (2006.01)
*A61K 39/39* (2006.01)

(52) U.S. Cl.
CPC ....... *A61K 39/39* (2013.01); *A61K 2039/55516* (2013.01); *A61K 2039/55561* (2013.01)

(58) Field of Classification Search
CPC ....... A61K 38/00; A61K 39/00; A61K 39/39; A61K 45/06; A61K 2039/58; A61K 2300/00; C07K 1/00; C07K 16/28; C07K 16/2875
See application file for complete search history.

(56) References Cited

FOREIGN PATENT DOCUMENTS

| WO | 03/014335 A1 | 2/2003 |
|---|---|---|
| WO | 2005/012509 A2 | 2/2005 |

OTHER PUBLICATIONS

Napolotani et al., 2005. Nature Immunology. vol. 6(8): 769-776.*
Napolitani et al., (Nature Immunol. 2005. vol. 6(8): 769-776.*
Whitmore et al., (Cancer Res. 2004. vol. 64:5850-5860).*
Bagchi et al., (J of Immunology. 2007, vol. 178:1164-1171 Received for publication Jan. 26, 2006; Accepted for Publication Nov. 2, 2006).*
Anada et al., (Bioorganic & Medicinal Chemistry Letters. 2006. vol. 16. pp. 1301-1304; Available online Dec. 15, 2005).*

(Continued)

*Primary Examiner* — Ja'Na Hines
(74) *Attorney, Agent, or Firm* — Locke Lord LLP; Gabriel J. McCool

(57) ABSTRACT

The present invention provides immunostimulatory combinations of TLR ligands and therapeutic and/or prophylactic methods that include administering an immunostimulatory combination to a subject. In general, the immunostimulatory combinations described herein can provide an increased immune response compared to other immunostimulatory combinations and/or compositions.

10 Claims, 15 Drawing Sheets

(56) References Cited

OTHER PUBLICATIONS

Kornbluth et al., (J. of Leukocyte Biology. vol. 80. Published Aug. 24, 2006).*

Warger et al., (Immunobiology. Jul. 2006. vol. 108(2):544-550. Published online Mar. 2006).*

Napolitani et al., (Nature Immunol. vol. 6(8):769-776).*

Napolitani Giorgio et al., "Selected Toll-like receptor agonist combinations synergistically trigger a T helper type 1—polarizing program in dendritic cells", Nature Immunology, vol. 6, No. 8, Aug. 2005, pp. 769-776.

Aranya et al., "MyD88-dependent and MyD88-independent pathways in synergy, priming, and tolerance between TLR agonists", Journal of Immunology, vol. 178, No. 2, Jan. 2007, pp. 1164-1171.

Whitmore et al., "Synergistic Activation of Innate Immunity by Double-Stranded RNA and CPG DNA Promotes Enhanced Antitumor Activity", Cancer Research, vol. 64, No. 16, Aug. 2004, pp. 5850-5860.

Warger et al., "Synergistic activation of dendritic cells by combined Toll-like receptor ligation induces superior CTL Responses in vivo", Blood, vol. 108, No. 2, Jul. 2006, pp. 544-550.

Qing et al., "Toll-like receptor ligands synergize through distinct dendritic cell pathways to induce T cell responses: Implications for vaccines", Proceedings of the National Acadamy of Sciences of the United States of America, vol. 105, No. 42, Oct. 2008, pp. 16260-16265.

Trinchieri et al., "Cooperation of Toll-like receptor signals in innate immune defence", Nature Reviews Immunology, vol. 7, No. 3, Mar. 2007, pp. 179-190.

Verkijk et al., "Polyriboinosinic polyribocytidylic acid (poly(I:C)) induces stable maturation of functionally active human dendritic cells", Journal of Immunology, vol. 163, No. 1, Jul. 1999, pp. 57-61.

Bohnenkamp et al., "Synergism of Toll-like receptor-induced interleukin-12p70 secretion by monocyte-derived dendritic cells is mediated through p38 MAPK and lowers the threshold of T-helper cell type I responses", Cellular Immunology, vol. 247, No. 2, Oct. 2007, pp. 72-84.

Vanhoutte et al., "Toll-like receptor (TLR)2 and TLR3 synergy and cross-inhibition in murine myeloid dendritic cells", Immunology Letters, vol. 116, No. 1, Dec. 2007, pp. 86-94.

Dillon et al., "A Toll-Like Receptor 2 Ligand Stimulates Th2 Responses In Vivo, via Induction of Extracellular Signal-Regulated Kinase Mitogen-Activated Protein Kinase and c-Fos in Dendritic Cells", The Journal of Immunology, 172: 4733-4743 (2004).

Zhu, Q. et al., "Using 3 TLR ligands as a combination adjuvant induces qualitative changes in T cell responses needed for antiviral protection in mice", *J. Clin. Invest.* 120:607-616 (2010).

* cited by examiner

IMMUNOSTIMULATORY COMBINATIONS OF TLR LIGANDS AND METHODS OF USE

RELATED APPLICATIONS

This application is a 35 U.S.C. §371 U.S. national entry of International Application PCT/US2008/011236 (WO 2009/088401) having an International filing date of Sep. 24, 2008 which claims the benefit of U.S. Provisional application No. 60/995,212, filed on Sep. 24, 2007. The entire contents of each of the aforementioned applications are hereby incorporated herein by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by the Intramural Research Program of the NIH, National Cancer Institute, Center for Cancer Research. This research has been funded in part with Federal funds from the National Cancer Institute, NIH, and the NIH Intramural AIDS Targeted Antiviral Program (IATAP). The government has certain rights to this invention.

FIELD OF THE INVENTION

The present invention relates generally to methods and compositions for modulating an immune response.

BACKGROUND OF THE INVENTION

Animals have evolved to possess a variety of innate mechanisms to protect themselves against foreign substances such as microbes. These include physical barriers, phagocytic cells in the blood and tissues, natural killer cells and various blood-borne molecules. Some of these mechanisms are present prior to exposure to infectious microbes or foreign substances. Additionally, they do not discriminate between most foreign substances. And generally, they are not enhanced to any great extent by exposure to the foreign substance. As a result, these mechanisms are the host's first line of defense against invasion by foreign substances. Although limited in some sense, they are also the only line of defense until the adaptive or acquire immune response is triggered. The ability of a subject to mount an innate immune response may vary from subject to subject. These differences can control whether an infection is resolved without any or at least substantial symptoms, or whether the subject experiences an infection and its associated myriad of symptoms. Given its importance as a first line of defense, therapies which promote innate immunity are desirable. For example, a more robust innate immune response would overcome the need for more diverse antibiotics, a consideration given the emergence of multi-resistant microbes.

Development of innate and adaptive immunity critically depends on the engagement of pattern recognition receptors (PRRs), which specifically detect microbial components named pathogen- or microbe-associated molecular patterns (PAMPs or MAMPs) (1-4). Toll-like receptors (TLRs) represent an important group of PRRs that can sense PAMPs or MAMPs once in the body. TLRs are widely expressed by many types of cells, for example cells in the blood, spleen, lung, muscle and intestines.

New drugs or therapies that act by stimulating the immune system, or alternatively inhibiting certain aspects of the immune system, may be useful for treating various diseases or disorders, for example viral diseases, neoplasia, or allergies, and may also have use as vaccine adjuvants. However, although adjuvants have been suggested for use in vaccine compositions, there is an unmet need for adjuvants that can effectively enhance immune response.

SUMMARY OF THE INVENTION

The present invention provides immunostimulatory combinations of TLR ligands and therapeutic and/or prophylactic methods that include administering an immunostimulatory combination to a subject. In general, the immunostimulatory combinations can provide an increased immune response compared to other immunostimulatory combinations and/or compositions.

In one aspect, the invention provides immunostimulatory compositions comprising a combination of two or more Toll Like Receptor (TLR) agonists. In one embodiment, each TLR agonist alone induces limited or no immune response. For example, low doses of each TLR agonist are used at which each TLR agonist alone induces a limited or no IR.

In another aspect, the invention provides immunostimulatory compositions comprising a combination of two or more Toll Like Receptor (TLR) agonists, wherein at least one TLR agonist is a TLR3 agonist.

In a further aspect, the invention provides immunostimulatory compositions comprising a combination of two or more Toll Like Receptor (TLR) agonists, wherein at least one TLR agonist is a TLR3 agonist, and at least another TLR agonist is a TLR2 agonist.

In another aspect, the invention provides immunostimulatory compositions comprising a combination of two or more Toll Like Receptor (TLR) agonists, wherein at least one TLR agonist is a TLR3 agonist, and at least another TLR agonist is a TLR9 agonist.

In another aspect the invention provides immunostimulatory compositions comprising a combination of three or more Toll Like Receptor (TLR) agonists, wherein at least one TLR agonist is a TLR3 agonist, at least one TLR agonist is a TLR2 agonist, and at least one TLR agonist is a TLR9 agonist.

In one embodiment of any of the above aspects, the immunostimulatory compositions further comprises one or more antigens. In another embodiment, the one or more antigens is conjugated to a TLR agonist.

In another aspect, the invention features an immunostimulatory composition comprising a combination of two or more Toll Like Receptor (TLR) agonists and one or more antigens.

In another aspect, the invention features an immunostimulatory composition comprising a combination of two or more Toll Like Receptor (TLR) agonists, wherein at least one TLR agonist is a TLR3 agonist, and at least another TLR agonist is a TLR2 agonist and one or more antigens.

In a further aspect, the invention features an immunostimulatory composition comprising a combination of two or more Toll Like Receptor (TLR) agonists, wherein at least one TLR agonist is a TLR3 agonist, and at least one TLR agonist is a TLR9 agonist and one or more antigens.

In another aspect, the invention features an immunostimulatory composition comprising a combination of three or more Toll Like Receptor (TLR) agonists, wherein at least one TLR agonist is a TLR3 agonist, at least one TLR agonist is a TLR2 agonist, and at least one TLR agonist is a TLR9 agonist and one or more antigens.

In one embodiment of any one of the above-mentioned aspects, the immunostimulatory composition is effective for inducing an immune response to the antigen in a subject immunized with the immunostimulatory composition.

In another embodiment of any one of the above-mentioned aspects, the antigen comprises a tumor antigen, a viral antigen, a bacterial antigen, a fungal antigen, a parasitic antigen, an alloantigen, or a xenoantigen.

In a further embodiment, the viral antigen is selected from the group consisting of: HIV, Hepatitis C, and human papilloma virus (HPV).

In another further embodiment, the TLR agonists are selected from the group consisting of agonists for: TLR1, TLR2, TLR3, TLR4, TLR5, TLR6, TLR7, TLR8, TLR9, TLR10 and TLR11.

In one embodiment of any one of the above-mentioned aspects, the TLR agonist is derived from a microbe, derived from a plant, derived from an animal, or is synthetic. In a particular embodiment, the TLR agonist derived from a microbe is selected from macrophage activating lipoproteins, double stranded RNA or CpG oligodeoxynucleotides. In another particular embodiment, the double stranded RNA is PolyI:C.

In another embodiment of any one of the above-mentioned aspects, the ratio of each of the TLR agonists to another TLR agonist is 1:1, 1:5, 1:10, 1:20, 1:40, 1:50, 1:60, 1:70, 1:80, 1:90, 1:100, 1:200, 1:300, 1:400, 1:500, 1:600, 1:800, 1:1000, 1:1200, 1:1400, 1:1600, 1:1800, 1:2000. In certain particular embodiment, the ratio of each of the TLR agonists to another TLR agonist is in the range of 1:1 to 1:2000.

In another embodiment of any one of the above-mentioned aspects, each of the TLR agonists is between about 0.1 μg-100 μg % weight of the composition.

In still another embodiment of any one of the above-mentioned aspects, each one of the TLR agonists alone induces limited to no immune response.

In another aspect, the invention features methods of activating dendritic cells (DCs) in a subject comprising administering to the subject a combination of two or more Toll Like Receptor (TLR) agonists that are effective to activate dendritic cells (DCs).

In a further aspect, the invention features methods of activating dendritic cells (DCs) in a subject comprising administering to the subject a combination of two or more Toll Like Receptor (TLR) agonists, wherein at least one TLR agonist is a TLR3 agonist, that are effective to activate dendritic cells (DCs).

In another aspect, the invention features methods of activating dendritic cells (DCs) in a subject comprising: administering to the subject a combination of two or more Toll Like Receptor (TLR) agonists, wherein at least one TLR agonist is a TLR3 agonist, and at least another TLR agonist is a TLR2 agonist, that are effective to activate dendritic cells (DCs).

In another aspect, the invention features methods of activating dendritic cells (DCs) in a subject comprising administering to the subject a combination of two or more Toll Like Receptor (TLR) agonists, wherein at least one TLR agonist is a TLR3 agonist, and at least one TLR agonist is a TLR9 agonist, that are effective to activate dendritic cells (DCs).

In still another aspect, the invention features methods of activating dendritic cells (DCs) in a subject comprising administering to the subject a combination of three or more Toll Like Receptor (TLR) agonists, wherein at least one TLR agonist is a TLR3 agonist, at least one TLR agonist is a TLR2 agonist, and at least one TLR agonist is a TLR9 agonist, that are effective to activate dendritic cells (DCs).

In one embodiment of any one of the above-mentioned aspects, each one of the TLR agonists alone induces little or no immune response immune response.

In another embodiment of any one of the above-mentioned aspects, the method of activating dendritic cells (DCs) in a subject further comprises co-administering one or more antigens.

In one embodiment, the antigen comprises a tumor antigen, a viral antigen, a bacterial antigen, a fungal antigen, a parasitic antigen, an alloantigen, or a xenoantigen. In another embodiment, the viral antigen is selected from the group consisting of human immunodeficiency virus (HIV), Hepatitis C, and human papilloma virus (HPV).

In another embodiment of any one of the above-mentioned aspects, activating DCs further comprises induction of a T cell response. In one embodiment, induction of a T cell response increases production of inflammatory cytokines and chemokines.

In another embodiment of any one of the above-mentioned aspects, activating of DCs further comprises activation of a MyD88 signaling pathway.

In another aspect, the invention features a method of activating antigen-specific $CD8^+$ T cells in a subject comprising administering to the subject a combination of two or more Toll Like Receptor (TLR) agonists that are effective to activate antigen-specific $CD8^+$ T cells.

In another aspect, the invention features a method of activating antigen-specific $CD8^+$ T cells in a subject comprising administering to the subject a combination of two or more Toll Like Receptor (TLR) agonists, wherein at least one TLR agonist is a TLR3 agonist, that are effective to activate antigen-specific $CD8^+$ T cells.

In a further aspect, the invention features a method of activating antigen-specific $CD8^+$ T cells in a subject comprising administering to the subject a combination of two or more Toll Like Receptor (TLR) agonists, wherein at least one TLR agonist is a TLR3 agonist, and at least one TLR agonist is a TLR2 agonist, that are effective to activate antigen-specific $CD8^+$ T cells.

In another aspect, the invention features a method of activating antigen-specific $CD8^+$ T cells in a subject comprising: administering to the subject a combination of two or more Toll Like Receptor (TLR) agonists, wherein at least one TLR agonist is a TLR3 agonist, and at least one TLR agonist is a TLR9 agonist, that are effective to activate antigen-specific $CD8^+$ T cells.

In still another aspect, the invention features a method of activating antigen-specific $CD8^+$ T cells in a subject comprising administering to the subject a combination of three or more Toll Like Receptor (TLR) agonists, wherein at least one TLR agonist is a TLR3 agonist, at least one TLR agonist is a TLR2 agonist, and at least one TLR agonist is a TLR9 agonist, that are effective to activate antigen-specific $CD8^+$ T cells.

In one embodiment of any of the above-mentioned aspects, each one of the TLR agonists alone induces limited or no immune response. For example, low doses of each TLR agonist are used at which each TLR agonist alone induces a limited or no IR.

In another embodiment of any of the above-mentioned aspects, the method of activating antigen-specific $CD8^+$ T cells in a subject further comprises co-administering one or more antigens.

In one embodiment, the antigen comprises a tumor antigen, a viral antigen, a bacterial antigen, a fungal antigen, a parasitic antigen, an alloantigen, or a xenoantigen. In another embodiment, the viral antigen is selected from the group consisting of: HIV, Hepatitis C, and human papilloma virus (HPV).

In a further embodiment of any of the above-mentioned aspects, the other one or more TLR agonists are selected from the group consisting of agonists for TLR1, TLR2, TLR3, TLR4, TLR5, TLR6, TLR7, TLR8, TLR9, TLR10, and TLR11.

In another further embodiment of any of the above-mentioned aspects, the TLR agonist is derived from a microbe, derived from a plant, derived from an animal, or is synthetic.

In a particular embodiment, the TLR agonist derived from a microbe is selected from macrophage activating lipoproteins, double stranded RNA or CpG oligodeoxynucleotides. In a related embodiment, the double stranded RNA is PolyI:C.

In another aspect, the invention features a method of treating a condition in a subject comprising administering to the subject a combination of two or more Toll Like Receptor (TLR) agonists that are effective for stimulating a cell-mediated immune response and treating the condition in the subject.

In a further aspect, the invention features a method of treating a condition in a subject comprising administering to the subject a combination of two or more Toll Like Receptor (TLR) agonists, wherein at least one TLR agonist is a TLR3 agonist that are effective for stimulating a cell-mediated immune response and treating the condition in the subject.

In a further aspect, the invention features a method of treating a condition in a subject comprising administering to the subject a combination of two or more Toll Like Receptor (TLR) agonists, wherein at least one TLR agonist is a TLR3 agonist, and at least one TLR agonist is a TLR2 agonist that are effective for stimulating a cell-mediated immune response and treating the condition in the subject.

In another aspect, the invention features a method of treating a condition in a subject comprising administering to the subject a combination of two or more Toll Like Receptor (TLR) agonists, wherein at least one TLR agonist is a TLR3 agonist, and at least one TLR agonist is a TLR9 agonist that are effective for stimulating a cell-mediated immune response and treating the condition in the subject.

In another further aspect, the invention features a method of treating a condition in a subject comprising: administering to the subject a combination of two or more Toll Like Receptor (TLR) agonists, wherein at least one TLR agonist is a TLR3 agonist, at least one TLR agonist is a TLR2 agonist, and at least one TLR agonist is a TLR9 agonist that are effective for stimulating a cell-mediated immune response and treating the condition in the subject.

In one embodiment of any of the above aspects, the condition is selected from the group comprising: neoplastic disease, viral infection, bacterial infection, fungal infection, allergy, and autoimmune disease. In a particular embodiment, the neoplastic disease is cancer. In another particular embodiment, the viral disease is selected from the group consisting of: HIV, herpes simplex virus (HSV), HPV, hepatitis C virus (HCV), hepatits B virus (HBV), influenza, West Nile Virus, and ebola.

In another embodiment of any of the above-mentioned aspects, administering the TLR agonists provides prophylactic treatment. In another embodiment of any of the above-mentioned aspects, administering the TLR agonists provides therapeutic treatment.

In another aspect, the invention features a method for treating or preventing an allergic response comprising administering to a subject at risk of developing an allergic response an immunostimulatory composition comprising a combination of two or more Toll Like Receptor (TLR) agonists, thereby treating or preventing the allergic response.

In one embodiment, the immunostimulatory composition further comprises an antigen. In another embodiment, the allergic response is directed to the antigen.

In another aspect, the invention features a method for preventing an autoimmune response in a subject comprising administering to a subject in need thereof an effective amount of an immunostimulatory composition comprising a combination of two or more Toll Like Receptor (TLR) agonists.

In one embodiment, the immunostimulatory composition further comprises one or more antigens.

In another embodiment, the autoimmune response is directed to the antigen.

In another aspect, the invention features a method for treating or preventing a symptom of an autoimmune disease comprising administering to a subject at risk of developing an autoimmune disease an effective amount of an immunostimulatory composition comprising a combination of two or more Toll Like Receptor (TLR) agonists and an antigen, wherein said autoimmune disease involves an immune response to the antigen, thereby treating or preventing a symptom of an autoimmune disease.

In one embodiment of any of the above-mentioned aspects, at least one TLR agonist is a TLR3 agonist.

In another embodiment of any of the above-mentioned aspects, each TLR agonist alone induces limited or no immune response. For example, low doses of each TLR agonist are used at which each TLR agonist alone induces a limited or no IR.

In another aspect, the invention features a pharmaceutical composition comprising a combination of two or more Toll Like Receptor (TLR) agonists with a carrier.

In another aspect, the invention features a pharmaceutical composition comprising a combination of two or more Toll Like Receptor (TLR) agonists with a carrier.

In still another aspect, the invention features a pharmaceutical composition comprising a combination of two or more Toll Like Receptor (TLR) agonists, wherein at least one TLR agonist is a TLR3 agonist, and at least another TLR agonist is a TLR2 agonist with a carrier.

In a further aspect, the invention features a pharmaceutical composition comprising a combination of two or more Toll Like Receptor (TLR) agonists, wherein at least one TLR agonist is a TLR3 agonist, and at least another TLR agonist is a TLR9 agonist with a carrier.

In another further aspect, the invention features a pharmaceutical composition comprising a combination of three or more Toll Like Receptor (TLR) agonists, wherein at least one TLR agonist is a TLR3 agonist, at least another TLR agonist is a TLR2 agonist, and at least another TLR agonist is a TLR9 agonist with a carrier.

In one embodiment of any of the above-mentioned aspects, the combination of TLR agonists induces an immune response.

In another embodiment of any of the above-mentioned aspects, each TLR agonist alone induces limited or no immune response. For example, low doses of each TLR agonist are used at which each TLR agonist alone induces a limited or no IR.

In a further embodiment of any of the above-mentioned aspects, the pharmaceutical composition further comprises one or more antigens.

In one embodiment, the antigen is conjugated to a TLR agonist.

In another embodiment, the antigen comprises a tumor antigen, a viral antigen, a bacterial antigen, a fungal antigen, a parasitic antigen, an alloantigen, or a xenoantigen.

In another aspect, the invention features a kit comprising an immunostimulatory composition comprising of two or more Toll Like Receptor (TLR) agonists, and instructions for use.

In one embodiment, the kit further comprises one or more antigens.

These and other objects of the invention will be described in further detail in connection with the detailed description of the invention.

DETAILED DESCRIPTION OF THE INVENTION

Figure 1:
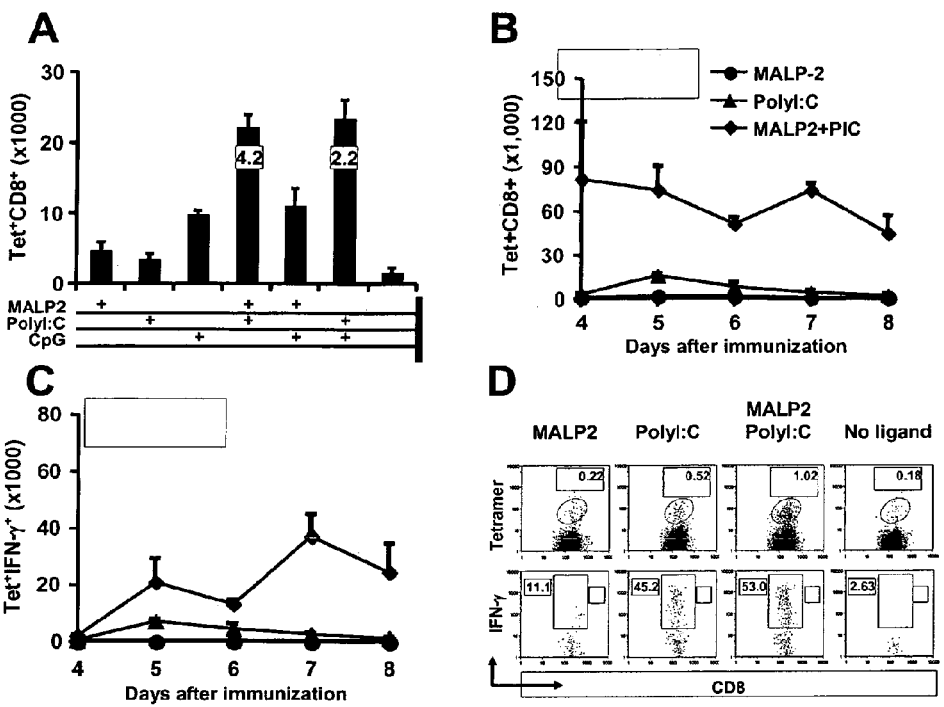
FIGS. 1(A-D) shows that TLR ligands act synergistically to prime T cells in vivo. BALB/c mice were immunized subcutaneously by footpad injection for 3 consecutive days with a mixture of PCLUS3-18IIIB containing the P18I10 epitope and TLR ligands, MALP-2, PolyI: C and CpG singly or pairwise (see Experimental Procedures for doses). Cells were isolated from paired popliteal lymph nodes (LNs) and stained with H-2Dd/P18I10 tetramers for flow cytometry to analyze antigen-specific CD8+ T cells. Panel (A) is a graph showing the total number of tetramer positive (tet+) CD8+ T cells at day 5 after the first immunization. Value on bars in all figures indicates a synergy between two ligands expressed as fold increase calculated by dividing the increase (subtracting the no ligand control) in the response to the paired ligands by the sum of the individual ligands. Panels (B) and (C) are graphs showing the results of time course studies of P18I10 tet+CD8+ T cells and IFN-g producing (IFN-g+) tet+CD8+T cells after immunization with peptide and MALP-2+PolyI: C. Numbers on the X axis indicate number of days after the first immunization. Panel (D) shows representative flow cytometry of P18I10 tet+CD8+ and IFN-g+tet+CD8+T cells out of CD8+ T cells (based on the tetramer gate) at day 5 after immunization.

The invention is better understood with the aid of the following definitions.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "agonist" as it is used herein relates to a ligand and receptor, comprises a molecule, combination of molecules, a complex, or a combination of reagents, that stimulates a receptor. For example, a toll like receptor (TLR) agonist can encompass a TLR ligand, a mutein or derivative of a TLR ligand, a peptide mimetic of a TLR ligand, a small molecule that mimics the biological function of a TLR ligand, or an antibody that stimulates a TLR receptor. As used herein, a TLR ligand is any molecule that binds to a TLR (i.e., a Toll-like receptor). In certain embodiments, the TLR ligand may be from a microbial component. In other certain embodiments, the TLR ligand may be selected from macrophage activating lipoproteins, Poly I: C or CpG oligodeoxynucleotides.

The term "allergic response" is meant to refer to a type of immune response. An allergic response can be caused by an oversensitive immune system that reacts to allergens. Allergens may be harmless in most people (i.e. do not cause an allergic response), but cause an allergic response in a sensitive individual. Exemplary allergens include pollen, mold, pet dander, and dust, certain foods and drugs. Allergic reactions can also be caused by insect bites, jewelry, cosmetics, temperature, sunlight, or other physical stimuli.

The term "autoimmune disease" is meant to refer to a disease that results from an immune response against ones own cells or tissues.

The tem "antigen" is meant to refer to any substance that is capable of raising an immune response. An antigen may raise, for example, a cell-mediated and/or humoral immune response in a subject organism. Alternatively, an antigen may raise a cellular immune response (e.g., immune cell maturation, production of cytokines, production of antibodies, etc.) when contacted with immune cells. In certain embodiments, the antigen can be any material capable of raising a TH1 immune response, which may include one or more of, for example, a CD8+T cell response, an NK T cell response, a gamma/delta T cell response, or a TH1 antibody response. Suitable antigens include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived antigens, toxins or toxoids.

The term "effective amount" or "amount effective" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. An effective amount also encompasses an amount that results in a desired immune response.

The term "immune response" is meant to refer to how your body recognizes and defends itself against bacteria, viruses, and substances that appear foreign and harmful to the body. An immune response can refer to any of innate immunity; humoral immunity; cellular immunity; immunity; inflammatory response; acquired (adaptive) immunity The term "immunostimulatory" or "stimulating an immune response" is meant to include stimulation of cell types that participate in immune reactions and enhancement of an immune response to a specific antigenic substance. An immune response can be a "$T_H$ 1-type" immune response or a "$T_H$ 2-type" immune response. Th1-type immune responses are normally characterized by "delayed-type hypersensitivity" reactions to an antigen and activated macrophage function and can be detected at the biochemical level by increased levels of $T_H$ 1-associated cytokines such as IFN-gamma, IL-2, IL-12, and TNF-beta. $T_H$ 2-type immune responses are generally associated with high levels of antibody production, especially IgE antibody production and enhanced eosinophils numbers and activation, as well as expression of $T_H$ 2-associated cytokines such as IL-4, IL-5 and IL-13.

The term "conjugate" or "conjugated" is meant to refer to a complex in which a ligand and an antigen are coupled. In preferred embodiments, the ligand is a Toll-like Receptor (TLR) ligand. Such conjugate couplings include covalent and/or non-covalent linkages.

The term "dendritic cells" is meant to refer to antigen presenting cells (APCs) that are able to stimulate naïve T cells. Dendritic cells (DCs) are involved in the induction of T cell responses resulting in cell-mediated immunity. DCs occur in at least two lineages. The first lineage encompasses pre-DC1, myeloid DC1, and mature DC1. The second lineage encompasses $CD34^{++}CD45RA^{-}$ early progenitor multipotent cells, $CD34^{++}CD45RA^{+}$ cells, $CD34^{++}CD45RA^{++}CD4^{+}$ IL-3Ralpha$^{++}$ pro-DC2 cells, $CD4^{+}CD11c^{-}$ plasmacytoid pre-DC2 cells, lymphoid human DC2 plasmacytoid-derived DC2s, and mature DC2s The term "T cell response" is meant to include immune responses mediated by T-cells, including those generally responsible for clearance of intracellular pathogens, virus-infected cells, tumor cells, as well as those responsible for transplant rejection and autoimmunity.

The term "MyD88" (also known as myeloid differentiation primary response gene 88) is meant to refer to one of several myeloid differentiation primary response genes that are induced in murine M1 myeloblastic leukemia cells upon stimulation with IL-6. MyD88 is an adaptor protein that is involved in signaling triggered by various members of the interleukin-1 receptor (IL-1R)/Toll-like receptor (TLR) superfamily.

The term "MyD88 signaling pathway" is meant to refer to downstream signaling events affected by modulation of MyD88 activity. In certain embodiments, a role for MyD88 signaling has been shown in response to triggering of IL-1R, IL-18R, TLR2, TLR3, TLR4, TLR9.

The term "$CD8^{+}$ T cell" is meant to refer to a T-cell having on its surface the CD8 protein. CD8 T cells can recognize and destroy both tumor cells and pathogen-infected cells, for example cells that are infected by viruses such as HIV.

The term "stimulating an immune response" or "enhancing immune response" or "augmenting immune response" is meant any improvement in an immune response, including mucosal immune response, which has already been mounted by a mammal. By "inducing an immune response" is meant the initiation of an immune response, including mucosal immune response, against an antigen of interest in a mammal in which an immune response against the antigen of interest has not already been initiated. Both situations are included in this invention and words enhance, induce, potentiate, and augment will be used interchangeably. In both situations, the immune response can involve both the humoral and cell-mediated arms of the immune system. For further discussion of immune responses, see, e.g., Abbas et al. Cellular and Molecular Immunology, 3.sup.rd Ed., W. B. Saunders Co., Philadelphia, Pa. (1997). Those of ordinary skill in the art recognize that there are a variety of methods for assessing such enhancements, for example, humoral antibody measurements, cytokine measurements, assessing animal health or well-ness, clinical protection from disease, and measuring cell mediated changes in immunity.

The term "subject" is meant to refer to a vertebrate, preferably a mammal, more preferably a human. Mammals include, but are not limited to, humans, primates, farm animals, sport animals, rodents and pets.

The term "subject at risk", as used herein, is meant to refer to a subject who has a higher than normal risk of developing an infection, or a cancer, or an allergy. A subject at risk in certain embodiments will benefit from treatment with two or more TLR agonists of the invention.

The term "immunostimulatory composition as used herein refers to a composition that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Immunostimulatory compositions may, in certain examples, stimulate innate immune responses. In certain preferred embodiments, the immunostimulatory composition comprises two or more TLR agonists. In certain preferred embodiments, the immunostimulatory composition includes an antigen. In addition to the antigen, the immunostimulatory composition may comprise other components such as, for example, one or more adjuvants or a carrier.

The term "effective amount" or a "sufficient amount" of a substance is meant to refer to that amount sufficient to effect beneficial or desired results, including clinical results, and, as such, an "effective amount" depends upon the context in which it is being applied. An effective amount can be administered in one or more administrations.

The term "suppression" or "inhibition" of a response or parameter includes decreasing that response or parameter when compared to otherwise same conditions except for a condition or parameter of interest, or alternatively, as compared to another condition.

The term "treating" a disease or disorder means that the extent and/or undesirable clinical manifestations of a disorder or a disease state are lessened and/or time course of the progression is slowed or lengthened, as compared to not treating the disorder. Especially in the autoimmune disease context, as is well understood by those skilled in the art, palliation might occur upon regulation or reduction of the unwanted immune response. Further, palliation does not necessarily occur by administration of one dose, but often occurs upon administration of a series of doses. Thus, an amount sufficient to palliate a response or disorder may be administered in one or more administrations.

As used herein, the term "Toll Like Receptor (TLR)" is meant to refer in general to any Toll-like receptor of any species of organism. A TLR may be from any mammalian species. TLRs have been identified in various mammalian species including, but not limited to, for example, humans, guinea pigs, and mice. A specific TLR may be identified with additional reference to species of origin (e.g., human, murine, etc.), a particular receptor (e.g., TLR2, TLR3, TLR9, etc.), or both.

In the invention described herein, novel combinations of TLR receptors are described. The novel combinations of TLR receptors described herein can include two or more, for example in exemplary embodiments three, TLR receptors. In exemplary embodiments, combinations of TLR 2, 3 and 9 are employed in vivo and in vitro, and a novel mechanism for TLR synergy in terms of both signaling pathways and cytokine combinations is described.

Toll Like Receptors (TLRs)

Toll-like receptors (TLRs) are a family of germline-encoded transmembrane proteins that facilitate pathogen recognition and activation of the innate immune system. (Hoffmann J A et al., Science 284, 1313-1318 (1999); Rock F L et al., Proc Natl Acad Sci USA 95:588-593 (1998)). Toll-like receptors (TLRs) are pattern recognition receptors (PRRs), and are expressed by cells of the innate immune system, including macrophages, dendritic cells and NK cells. Examples of known ligands for TLRs include gram positive bacteria (TLR-2), bacterial endotoxin (TLR-4), flagellin protein (TLR-5), bacterial DNA (TLR-9), double-stranded RNA and poly I:C (TLR-3), and yeast (TLR-2). Other ligands that bind an endocytic pattern recognition receptors, a scavenger receptor or a mannose-binding receptor may also be contemplated by the instant invention. TLRs engage conserved pathogen-derived ligands and subsequently activate the TLR/IL-1R signal transduction pathway to induce a variety of effector genes. (Medzhitov R et al., Mol Cell 2:253-258 (1998); Muzio M et al., J Exp Med 187:2097-2101 (1998)).

Toll-like receptors (TLRs) represent an important group of PRRs that can sense PAMPs or MAMPs once in the body. They are widely expressed in blood, spleen, lung, muscle and intestines (5-7) by many types of cells, notably dendritic cells (DCs) but also macrophages, epithelial cells, and lymphocytes (8, 9).

Whereas some TLRs located on the cell surface are specific for microbial lipids and proteins (10-16), others associated with endosomal compartments inside cells are specific for nucleic acids (17-21). Ligation of the TLRs by their specific ligands results in conformational changes in the receptors, leading to downstream signal transduction that primarily involves MyD88- and TRIF-dependent pathways (3, 22). Except for TLR3, all other TLRs can signal through the MyD88 pathway to induce proinflammatory cytokines that involve activation of intracellular protein kinase cascades including IB kinase (IKK)-NF-B, and extracellular signal-regulated protein kinase (ERK), c-Jun N-terminal kinase (JNK) and p38 mitogen-activation protein kinases (MAPKs) (3, 23, 24). The TRIF pathway, independent of MyD88, is utilized by both TLR3 and TLR4 and mediates the induction of type I interferons (10, 25).

TLR ligands are often found multiply in different types of pathogens. It was reasoned that the immune system might have evolved to recognize selective combinations of these ligands in a synergistic way, in order to induce an appropriate immune response against the infecting microorganism (26, 27). TLR3 and 7 synergize with each other in inducing DCs isolated from peripheral blood to produce proinflammatory cytokines and chemokines (28, 29), and to activate TCR transgenic T cells with appropriate antigen specificity (29). TLR3 and 4 each could synergize with TLR7/8 and 9 to amplify IL-12 production by DCs in vitro, resulting in an enhancement of the Th1 T cell response (26). Likewise did the triple combination of TLR3, 4 and 7 (30). Furthermore, septic shock and inflammatory autoimmune diseases developed due to profound inflammation induced by triggering multiple TLRs, namely 2, 3 and 4 (30-33). However, in the past it was not clear whether the TLR synergies follow a logical pattern, and what molecular mechanisms are responsible, or whether multiple TLRs will show synergy in vivo. However, as shown herein, multiple TLRs will show synergy in vivo.

MyD88

The MyD88 gene was originally described as one of several myeloid differentiation primary response genes that are induced in murine M1 myeloblastic leukemia cells upon stimulation with IL-6. It is an exclusively cytosolic protein that functions as a unique adaptor for members of the type I interleukin-1 receptor (IL-1R)/Toll like receptor (TLR) family. The MyD88 protein has a modular structure. At its N-terminus, it has a "death domain" (DD) similar to the cytoplasmic signaling domains found in many members of the tumor necrosis factor (TNF) receptor superfamily. Its C-terminal domain is conserved in all members of the TLR/IL-1R super family and is, therefore, termed the "Toll/IL-1R" (TIR) domain. Both domains are required for MyD88 homodimerization and are separated by a short intermediate domain (ID) of unknown function. The TIR domain of MyD88 forms a homophilic interaction with the TIR domain of IL-1R and IL-1 Receptor accessory protein (IL-IRacP), IL-18R, and several TLRs, whereas the DD binds with the DD of both IL-1 receptor associated kinase (IRAK) and IRAK-2. Interaction with MyD88 triggers IRAK phosphorylation. Phosphorylated IRAK leaves the receptor complex and associates with TNF receptor-associated factor 6 (TRAF 6), which forms a molecular link to activation of NF-KB and c-jun N-terminal kinase (JNK). Targeted disruption of the MyD88 gene showed unambiguously the importance of MyD88 in IL-1, IL-18 and TLR (including LPS) signaling pathways. All IL-1 and IL-18 responses (including T-cell proliferation and induction of cytokines and acute phase proteins) were abrogated in MyD88.sup.−/− cells and no NF-.kappa.B or JNK activity was observed. MyD88.sup.−/− cells were resistant to LPS-induced endotoxic shock, but still showed delayed NF-.kappa.B translocation to the nucleus, which suggests redundancy at the level of MyD88 in the LPS-pathway.

MyD88 mRNA expression has been found to be constitutively expressed in many adult human tissues as a 2.6 kb mRNA species. Further, splice variants of MyD88 have been described, for example MyD88s, which encodes for a protein lacking the ID.

MyD88 is involved in signaling triggered by various members of the interleukin-1 receptor (IL-1R)/Toll-like receptor (TLR) superfamily. A role for MyD88 has been shown in response to triggering of IL-1R, IL-18R, TLR2, TLR3, TLR4, TLR9. IL-1 and IL-18 are pleiotropic cytokines which play a central role in the immune response and in many inflammatory diseases such as rheumatoid arthritis or septic shock. TLRs behave as receptors for various microbial products (including bacterial, viral, yeast-derived products). Members of the IL-1R/TLR superfamily, as well as MyD88 have been shown to play an important role in both innate and adaptive immune responses.

The role of MyD88 has been investigated in knockout mice. MyD88-deficient mice have defects in T cell proliferation as well as induction of acute phase proteins and cytokines in response to IL-1, and all IL-1- and IL-18-mediated functions examined in these mice were impaired (Adachi et al., Immunity, 1998, 9, 143 150). These MyD88-deficient mice also were shown to be have enhanced susceptibility to Staphlococcus aureus infection and proinflammatory cytokine secretion by peritoneal macrophages was completely abrogated (Takeuchi et al., J. Immunol., 2000, 165, 5392 5396).

Bacterial DNA and certain oligonucleotides containing unmethylated CpG dinucleotides can stimulate murine and human lymphocytes, leading to secretion of cytokines, expression of co-stimulatory molecules, and to an increase in antigen-presenting function. In addition to macrophages and other lymphocytes, dendritic cells (DCs) are also critical sentinels in antimicrobial responses. They show a highly potent ability, as antigen presenting cells, to stimulate naive T-cell activation. Exposure to microbial components such as lipopolysaccaharide and CpG DNA can induce DC maturation, characterized by cytokine production, up-regulation of co-stimulatory molecules, and an increased ability to activate T-cells. DCs from MyD88-deficient mice were used to show that CpG oligodeoxynucleotide DNA-induced DC maturation is MyD88-dependent (Akira et al., J. Endotoxin Res., 2000, 6, 383 387).

The MyD88 protein has a modular structure with an approximately 90-amino acid N-terminal "death domain" (DD), so called for its involvement hetero- or homodimeric protein interactions in apoptotic pathways, as well as its C-terminal domain Toll domain related to the cytoplasmic region of IL-1R and TLRs. The presence of these two domains suggests that MyD88 serves to connect an IL-1R or TLR with a downstream signaling mediator. A series of human MyD88 deletion mutants have been constructed to investigate the interactions between MyD88 and receptors upstream or signaling molecules downstream in 293T human embryonic kidney cells. Overexpression of an N-terminal deletion construct of MyD88 which leaves only the C-terminal region bearing homology to IL-1R acts as a dominant negative mutant, attenuating IL-1R-mediated NF-.kappa.B activation. Overexpression of a truncated version of MyD88 encoding only the death domain activates NF-kappaB These and similar deletion constructs have allowed the molecular ordering of signaling components in this pathway, and it was determined that MyD88 functions upstream of TRAF6 (Medzhitov et al., Mol. Cell, 1998, 2, 253 258; Muzio et al., Science, 1997, 278, 1612 1615).

Many signaling pathways involving DD-containing adaptor proteins lead to activation of the c-Jun N-terminal kinase (JNK)/stress-activated protein kinase pathway. Another series of death domain deletion mutations was generated as well as a point mutation which prevents dimerization of the death domain, and overexpression of these mutant constructs in 293T cells was found to inhibit IL-1 induced activation of NF-kappaB and JNK, suggesting that the death domain of MyD88 is critical for this activation (Burns et al., J. Biol. Chem., 1998, 273, 12203 12209).

The cytokines IL-1beta, interferon gamma (IFNgamma.), and TNF-alpha are believed to play an important role in the destruction of insulin-producing beta cells of the islets of Langerhans observed in type I diabetes. In particular, cytokine-induced production of nitric oxide has been shown to correlate with beta cell apoptosis and/or inhibition of insulin secretion beta cells overexpressing dominant negative MyD88 death domain point and deletion mutants had an attenuated level of IL-1beta/IFNgamma-induced nitric oxide generation, an increased resistance to apoptosis, and maintained their insulin secretory response to glucose, indicating that MyD88 mediates the cytokine-induced apoptosis pathway leading to diabetes (Dupraz et al., J. Biol. Chem., 2000, 275, 37672 37678).

Deletion mutants have further established the position of MyD88 in the innate immune signaling pathway serving as a host defense against pathogens. Bacterial lipopolysaccharide is a potent activator of macrophages, eliciting rapid morphological changes such as cell spreading, which is mediated by cell-matrix proteins. Macrophage spreading is dependent on the p38 MAP kinase pathway and cytokine production. Furthermore, the induction of spreading was inhibited by overexpression of a dominant negative MyD88 deletion mutant, indicating that spreading of macrophages is mediated by MyD88 (Schmidt et al., Mol. Cell. Biol., 2001, 21, 438 448).

Immunostimulatory Compositions

The invention described herein is based on the novel finding of a nonrandom, synergistic TLR interplay pattern in which triggering of TLR3 together with TLR2 and/or 9, but not the combination of TLR2 and 9, at suboptimal doses for each, synergistically activates DCs and leads to immediate induction of T cell responses. Thus, the present invention provides immunostimulatory combinations of TLR ligands and therapeutic and/or prophylactic methods that include administering an immunostimulatory combination to a subject. In general, the immunostimulatory combinations can provide an increased immune response compared to other immunostimulatory combinations and/or compositions.

Provided in the instant invention are immunostimulatory compositions. The term "immunostimulatory" or "stimulating an immune response" is meant to include stimulation of cell types that participate in immune reactions and enhancement of an immune response to a specific antigenic substance. An immune response can be a "TH 1-type" immune response or a "TH 2-type" immune response. Th1-type immune responses are normally characterized by "delayed-type hypersensitivity" reactions to an antigen and activated macrophage function and can be detected at the biochemical level by increased levels of TH 1-associated cytokines such as IFN-gamma, IL-2, IL-12, and TNF-beta. TH 2-type immune responses are generally associated with high levels of antibody production, especially IgE antibody production and enhanced eosinophils numbers and activation, as well as expression of TH 2-associated cytokines such as IL-4, IL-5 and IL-13. Thus, the invention provides, in certain preferred aspects, an immunostimulatory composition comprising a combination of two or more Toll Like Receptor (TLR) agonists.

In certain embodiments of the invention, the TLR agonists alone induce little or no immune response. By limited or no immune response is meant an immune response that is not sufficient to achieve an outcome in preventing, alleviating or treating a symptom, clinical sign or a disease. An important feature of the instant invention is that the TLR agonists that comprise the immunostimulatory compositions are present in amounts (ratios, percent weights) that, when combined with other TLR ligands, are sufficient to induce an immune response. In comparison, an equivalent amount of TLR ligand alone would induce a limited to no immune response.

Also included in the invention are immunostimulatory compositions that comprise a combination of two or more Toll Like Receptor (TLR) agonists, wherein at least one TLR agonist is a TLR3 agonist. In other aspects of the invention, the immunostimulatory composition comprises a combination of two or more Toll Like Receptor (TLR) agonists, wherein at least one TLR agonist is a TLR3 agonist, and at least another TLR agonist is a TLR2 agonist. In other aspects of the invention, the TLR agonist comprises a combination of two or more Toll Like Receptor (TLR) agonists, wherein at least one TLR agonist is a TLR3 agonist, and at least another TLR agonist is a TLR9 agonist. In still other aspects of the invention, the immunostimulatory composition comprises a combination of three or more Toll Like Receptor (TLR) agonists, wherein at least one TLR agonist is a TLR3 agonist, at least one TLR agonist is a TLR2 agonist, and at least one TLR agonist is a TLR9 agonist.

TLR agonists according to the invention can be any TLR agonists. The term agonist relates to a ligand and receptor, comprises a molecule, combination of molecules, a complex, or a combination of reagents, that stimulates a receptor. For example, a toll like receptor (TLR) agonist can encompass a TLR ligand, a mutein or derivative of a TLR ligand, a peptide mimetic of a TLR ligand, a small molecule that mimics the biological function of a TLR ligand, or an antibody that stimulates a TLR receptor. As used herein, a TLR ligand is any molecule that binds to a TLR (i.e., a Toll-like receptor). In certain embodiments, the TLR ligand may be from a microbial component. In other certain embodiments, the TLR ligand may be selected from macrophage activating lipoproteins, Poly I: C or CpG oligodeoxynucleotides. In certain preferred examples, TLR agonists are selected from the group consisting of agonists for TLR1, TLR2, TLR3, TLR4, TLR5, TLR6, TLR7, TLR8, TLR9, TLR10 and TLR11. The TLR agonist may be derived from a microbe, derived from a plant, derived from an animal, or in certain cases may be synthetic. When the TLR agonist is derived from a microbe, it may be selected from macrophage activating lipoproteins, double stranded RNA or CpG oligodeoxynucleotides. In certain preferred examples, the double stranded RNA is PolyI: C.

The immunostimulatory compositions are not limited to two TLR ligands or three TLR ligands, but can also comprise four, five or more TLR ligands.

Additionally, the immunostimulatory compositions can comprise TLR antagonists.

The immunostimulatory compositions of the invention can further comprise one or more antigens. In certain embodiments, the antigens can be conjugated to a TLR agonist or antagonist.

The immunostimulatory compositions can comprise a combination of two or more Toll Like Receptor (TLR) agonists and one or more antigens. The tem "antigen" is meant to refer to any substance that is capable of raising an immune response. An antigen may raise, for example, a cell-mediated and/or humoral immune response in a subject organism. Alternatively, an antigen may raise a cellular immune response (e.g., immune cell maturation, production of cytokines, production of antibodies, etc.) when contacted with immune cells. In certain embodiments, the antigen can be any material capable of raising a T$_H$1 immune response, which may include one or more of, for example, a CD8$^+$T cell response, an NK T cell response, a gamma/delta T cell response, or a T$_H$1 antibody response.

Accordingly, the immunostimulatory compositions that comprise antigens can comprise a combination of two or more Toll Like Receptor (TLR) agonists, wherein at least one TLR agonist is a TLR3 agonist, and at least another TLR agonist is a TLR2 agonist and an antigen. The immunostimulatory compositions that comprise antigens can comprise a combination of two or more Toll Like Receptor (TLR) agonists, wherein at least one TLR agonist is a TLR3 agonist, and at least one TLR agonist is a TLR9 agonist and one or more antigens. The immunostimulatory compositions that comprise antigens can comprise a combination of three or more Toll Like Receptor (TLR) agonists, wherein at least one TLR agonist is a TLR3 agonist, at least one TLR agonist is a TLR2 agonist, and at least one TLR agonist is a TLR9 agonist and one or more antigens.

Suitable antigens include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived antigens, toxins or toxoids.

The antigen can be any material capable of raising a T.sub.H1 immune response, which may include one or more of, for example, a CD8.sup.+ T cell response, an NK T cell response, a .gamma./.delta. T cell response, or a T.sub.H1 antibody response. Suitable antigens include but are not limited to peptides; polypeptides; lipids; glycolipids; polysaccharides; carbohydrates; polynucleotides; prions; live or inactivated bacteria, viruses or fungi; and bacterial, viral, fungal, protozoal, tumor-derived, or organism-derived antigens, toxins or toxoids, alloantigen or xenoantigen. Exemplary antigens according to the invention are HIV, Hepatitis C, human papilloma virus (HPV), and cancer antigens.

In certain embodiments, experimental antigens, for example recombinant proteins, glycoproteins, and peptides that do not raise a strong immune response, can be used in connection with adjuvant combinations of the invention. Exemplary experimental subunit antigens include those related to viral disease such as adenovirus, AIDS, chicken pox, cytomegalovirus, dengue, feline leukemia, fowl plague, hepatitis A, hepatitis B, HSV-1, HSV-2, hog cholera, influenza A, influenza B, Japanese encephalitis, measles, parainfluenza, rabies, respiratory syncytial virus, rotavirus, wart, and yellow fever.

The antigens may be for the treatment of autoimmune disorders. Autoimmune associated disorders for which the antigens of the invention may be employed to relieve the symptoms of, treat or prevent the occurrence or reoccurrence of include, for example, multiple sclerosis (MS), rheumatoid arthritis (RA), Sjogren syndrome, scleroderma, polymyositis, dermatomyositis, systemic lupus erythematosus, juvenile rheumatoid arthritis, ankylosing spondylitis, myasthenia gravis (MG), bullous pemphigoid (antibodies to basement membrane at dermal-epidermal junction), pemphigus (antibodies to mucopolysaccharide protein complex or intracellular cement substance), glomerulonephritis (antibodies to glomerular basement membrane), Goodpasture's syndrome, autoimmune hemolytic anemia (antibodies to erythrocytes), Hashimoto's disease (antibodies to thyroid), pernicious anemia (antibodies to intrinsic factor), idiopathic thrombocytopenic purpura (antibodies to platelets), Grave's disease, and Addison's disease (antibodies to thyroglobulin), and the like.

The autoantigens associated with a number of these diseases have been identified. For example, in experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis; thyroglobulin has been identified in experimental allergic thyroiditis (EAT) in mouse; acetyl choline receptor (AChR) in experimental allergic myasthenia gravis (EAMG); and myelin basic protein (MBP) and proteolipid protein (PLP) in experimental allergic encephalomyelitis (EAE) in mouse and rat. In addition, autoantigens have been identified in humans: type-II collagen in human rheumatoid arthritis; and acetyl choline receptor in myasthenia gravis.

In certain embodiments, the one or more antigens may be a cancer antigen or a tumor antigen. The terms cancer antigen and tumor antigen are used interchangeably and refer to an antigen that is differentially expressed by cancer cells. Therefore, cancer antigens can be exploited to differentially target an immune response against cancer cells. Cancer antigens may thus potentially stimulate tumor-specific immune responses. Certain cancer antigens are encoded, though not necessarily expressed, by normal cells. Some of these antigens may be characterized as normally silent (i.e., not expressed) in normal cells, those that are expressed only at certain stages of differentiation, and those that are temporally expressed (e.g., embryonic and fetal antigens). Other cancer antigens can be encoded by mutant cellular genes such as, for example, oncogenes (e.g., activated ras oncogene), suppressor genes (e.g., mutant p53), or fusion proteins resulting from internal deletions or chromosomal translocations. Still other cancer antigens can be encoded by viral genes such as those carried by RNA and DNA tumor viruses.

Examples of tumor antigens include MAGE, MART-1/Melan-A, gp100, Dipeptidyl peptidase IV (DPPUV), adenosine deaminase-binding protein (ADAbp), cyclophilin b, Colorectal associated antigen (CRC)-C017-1A/GA733, Carcinoembryonic Antigen (CEA) and its antigenic epitopes CAP-1 and CAP-2, etv6, aml1, Prostate Specific Antigen (PSA) and its antigenic epitopes PSA-1, PSA-2, and PSA-3, prostate-specific membrane antigen (PSMA), T-cell receptor/CD3-.zeta. chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, .alpha.-fetoprotein, E-cadherin, .alpha.-catenin, .beta.-catenin, .gamma.catenin, p120ctn, gp100.sup.Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2.

Cancers or tumors and specific tumor antigens associated with such tumors (but not exclusively), include acute lymphoblastic leukemia (etv6, aml1, cyclophilin b), B cell lymphoma (Ig-idiotype), glioma (E-cadherin, .alpha.-catenin, .beta.-catenin, .gamma.-catenin, p120ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-CO17-1A/GA733, APC), choriocarcinoma (CEA), epithelial cell cancer (cyclophilin b), gastric cancer (HER2/neu, c-erbB-2, ga733 glycoprotein), hepatocellular cancer (.alpha.-fetoprotein), Hodgkins lymphoma (Imp-1, EBNA-1), lung cancer (CEA, MAGE-3, NY-ESO-1), lymphoid cell-derived leukemia (cyclophilin b), melanoma (p5 protein, gp75, oncofetal antigen, GM2 and GD2 gangliosides, Melan-A/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (Imp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

Antigens may be peptides. In other embodiments, an antigen may be a lipid (e.g., sterol excluding cholesterol, fatty acid, and phospholipid), polysaccharide such as those used in *H. influenza* vaccines, ganglioside and glycoprotein. These can be obtained through several methods known in the art, including isolation and synthesis using chemical and enzymatic methods. In certain cases, such as for many sterols, fatty acids and phospholipids, the antigenic portions of the molecules are commercially available Immunostimulatory combinations of the invention that include an antigen may form an immunogenic composition. Such immunogenic compositions can contain additional pharmaceutically acceptable ingredients, excipients, carriers, and the like well known to those skilled in the art.

In certain embodiments, the immunostimulatory compositions are effective for inducing an immune response to the antigen in a subject immunized with the immunostimulatory composition.

In the immunostimulatory compositions as described herein the ratio of each of the TLR agonists to another TLR agonist is in the range of 1:1-1:2000. Any value within the range is possible, for example 1:2, 1:4, 1:6, 1:8, 1:10, 1:20, 1:30, 1:40, 1:50, 1:60, 1:70, 1:80, 1:90, 1:95, 1:100, 1:200, 1:300, 1:400, 1:500, 1:600, 1:800, 1:1000, 1:1200, 1:1400, 1:1600, 1:1800, 1:2000. In another embodiment, each of the TLR agonists is between about 0.1 µg-100 µg % weight of the composition.

Methods of the Invention

Included in the invention are methods of activating dendritic cells (DCs). Included are methods of activating dendritic cells (DCs) in a subject comprising administering to the subject a combination of two or more Toll Like Receptor (TLR) agonists that are effective to activate dendritic cells (DCs). The combination of two or more TLR agonists can be any combination of TLR agonists, where at least one TLR agonist is a TLR3 agonist, that are effective to activate dendritic cells (DCs). The combination of two or more TLR agonists can be any combination of TLR agonists, wherein at least one TLR agonist is a TLR3 agonist, and at least another TLR agonist is a TLR2 agonist. The combination of two or more TLR agonists can be any combination of TLR agonists, where at least one TLR agonist is a TLR3 agonist, and at least one TLR agonist is a TLR9 agonist, that are effective to activate dendritic cells (DCs). The combination of three or more TLR agonists can be any combination of TLR agonists, where at least one TLR agonist is a TLR3 agonist, at least one TLR agonist is a TLR2 agonist, and at least one TLR agonist is a TLR9 agonist, that are effective to activate dendritic cells (DCs).

In certain examples, activating DCs further comprises the induction of a T cell response.

In another embodiment of any one of the above-mentioned aspects, activating of DCs further comprises activation of a MyD88 signaling pathway.

The invention also features methods of activating antigen-specific $CD8^+$ T cells. Included are methods of activating antigen-specific $CD8^+$ T cells in a subject comprising administering to the subject a combination of two or more Toll Like Receptor (TLR) agonists that are effective to activate antigen-specific $CD8^+$ T cells. The combination of two or more TLR agonists can be any combination of TLR agonists, where at least one TLR agonist is a TLR3 agonist, that are effective to activate antigen-specific $CD8^+$ T cells. The combination of two or more TLR agonists can be any combination of TLR agonists, wherein at least one TLR agonist is a TLR3 agonist, and at least another TLR agonist is a TLR2 agonist. The combination of two or more TLR agonists can be any combination of TLR agonists, where at least one TLR agonist is a TLR3 agonist, and at least one TLR agonist is a TLR9 agonist, that are effective to antigen-specific $CD8^+$ T cells. The combination of three or more TLR agonists can be any combination of TLR agonists, whereat least one TLR agonist is a TLR3 agonist, at least one TLR agonist is a TLR2 agonist, and at least one TLR agonist is a TLR9 agonist, that are effective to activate antigen-specific $CD8^+$ T cells.

An important feature of the instant invention is that the TLR agonists are present in amounts (ratios, percent weights) that, when combined with other TLR agonists, are sufficient to induce an immune response. In comparison, an equivalent amount of TLR ligand alone would induce little to no immune response.

In certain examples, the TLR agonists that activate DCs or the TLR agonists that activate antigen-specific $CD8^+$ T cells as described herein are combined or co-administered with an antigen.

Exemplary antigens have been described herein.

In a further embodiment of any of the above-mentioned aspects, the other one or more TLR agonists are selected from the group consisting of agonists for TLR1, TLR2, TLR3, TLR4, TLR5, TLR6, TLR7, TLR8, TLR9, TLR10, and TLR11.

In another further embodiment of any of the above-mentioned aspects, the TLR agonist is derived from a microbe, derived from a plant, derived from an animal, or is synthetic.

In a particular embodiment, the microbial component is selected from macrophage activating lipoproteins, double stranded RNA or CpG oligodeoxynucleotides. In a related embodiment, the double stranded RNA is PolyI: C.

The invention also features methods for treating various conditions in a subject. The term "subject" is meant to refer to a vertebrate, preferably a mammal, more preferably a human. Mammals include, but are not limited to, humans, primates, farm animals, sport animals, rodents and pets.

In certain aspects, the invention features methods of treating a condition in a subject comprising administering to the subject a combination of two or more Toll Like Receptor (TLR) agonists that are effective for stimulating an immune response and treating the condition in the subject. The methods described herein feature combinations of two or more Toll Like Receptor (TLR) agonists. In certain combinations, at least one TLR agonist is a TLR3 agonist that is effective for stimulating an immune response and treating the condition in the subject. In other combinations, at least one TLR agonist is a TLR3 agonist, and at least another TLR agonist is a TLR2 agonist that are effective for stimulating an immune response and treating the condition in the subject. In other combinations, at least one TLR agonist is a TLR3 agonist, and at least another TLR agonist is a TLR9 agonist that are effective for stimulating an immune response and treating the condition in the subject. In other combinations, at least one TLR agonist is a TLR3 agonist, at least another TLR agonist is a TLR2 agonist, and at least another TLR agonist is a TLR9 agonist that are effective for stimulating an immune response and treating the condition in the subject.

The methods of the invention as described herein are useful for treating a condition in a subject. The condition can be selected from, but is not limited to, a neoplastic disease, viral infection, bacterial infection, fungal infection, parasitic infection, allergy, and autoimmune disease.

Additionally, the methods of the invention as described herein are useful for treating a subject at risk for a condition as described. Because innate immunity developed in part to protect a host against foreign antigens, such as for example, foreign pathogens, the methods of the invention are suited in some instances to treating subjects that are at risk of contacting foreign pathogens. In such subjects, the subject may be administered the immunostimulatory composition comprising a combination of two or more Toll Like Receptor (TLR) agonists on a regular basis when that risk is greatest. For example, the subject may be administered the immunostimulatory composition during allergy season or after exposure to a cancer causing agent. Additionally the immunostimulatory composition comprising a combination of two or more Toll Like Receptor (TLR) agonists may be administered to travelers prior to travel where they are at risk of exposure to infectious agents. Likewise the TLR ligand and immune stimulating complex may be administered to soldiers or civilians at risk of exposure to biowarfare.

A subject at risk, as used herein, is a subject who has a higher than normal risk of developing an infection, or a cancer, or an allergy. For example, a subject at risk of developing an infection may be a subject who is planning to travel to an area where a particular type of infectious agent is prevalent or it may be a subject who through lifestyle or medical procedures is exposed to bodily fluids which may contain infectious organisms or directly to the organism or even any subject living in an area where an infectious organism has been identified. Subjects at risk of developing infection also include general populations to which a medical agency recommends vaccination with a particular microbial antigen.

A subject having an infection is a subject that has been exposed to an infectious pathogen and has acute or chronic detectable levels of the pathogen in the body. An infectious disease, as used herein, is a disease arising from the presence of a foreign microorganism in the body. It is particularly important to develop effective innate immunity strategies and treatments to protect the body's mucosal surfaces, which are the primary site of pathogenic entry.

The infectious disease may be, but is not limited to, a bacterial infection, a viral infection, a fungal infection, a parasitic infection, or a mycobacterial infection, although it is not so limited.

Examples of bacterial infections include, but are not limited to, *Actinomyces* infection, an anthrax infection, a *Bacteriodes* infection, a *Borrelia* infection, a *Campylobacter* infection, a *Citrobacter* infection, a *Clostridium difficile* infection, a *Corynebacterium* infection, an *E. coli* infection, an *Enterobacter* infection, a *Gardnerella* infection, a *Haemophilus* infection, an *H. pylori* infection, a *Klebsiella* infection, a *Legionella* infection, a *Listeria* infection, a *Neisseria* infection, a *Nocardia* infection, a *Pasteurella* infection, a *Pneumococcus* infection, a *Proteus* infection, a *Pseudomonas* infection, a *Salmonella* infection, a *Shigella* infection, a *Spirillum* infection, a *Spirochaeta* infection, a *Staphylococcal* infection, a *Streptobacillus* infection, a *Streptococcal* infection, and a *Treponema* infection.

Examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria menin-* gitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus influenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, Rickettsia, and Actinomyces israeli.

Examples of viral infection include, but are not limited to, an adenovirus infection, a retrovirus infection, a rotavirus infection, etc. It may be but is not limited to a cytomegalovirus infection, an Epstein Barr virus infection, a hepatitis A virus infection, a hepatitis B virus infection, a hepatitis C virus infection, a Herpes simplex virus 1 infection, a Herpes simplex virus 2 infection, an HIV infection, a human papilloma virus infection, an influenza A virus infection, a monkey pox infection, a respiratory syncytial virus infection, a SARS infection a small pox infection, a varicella-zoster virus infection. In some embodiments, the infectious disease is a chronic infectious disease such as a chronic viral infection. Examples include hepatitis virus infection, human papilloma virus infection, HIV infection, and Herpes simplex virus infection.

In certain embodiments, the viral disease is selected from the group consisting of: HIV, HSV, HPV, HBV, influenza, West Nile Virus, and ebola.

Categories of viruses that have been found in humans include but are not limited to Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

In certain examples, the fungal infection may be, but is not limited to aspergillosis, blastomycosis, candidiasis, chromomycosis, crytococcosis, histoplasmosis, mycetoma infections, paracoccidioidomycosis, pseudallescheriasis, ringworm, and tinea versicolor infection. Examples of fungi include Cryptococcus neoformans, Histoplasma capsulatum, Coccidioides immitis, Blastomyces dermatitidis, Chlamydia trachomatis, and Candida albicans.

In certain examples, the mycobacterial infection may be, but is not limited to, M. tuberculosis and M. leprae.

In certain examples, the parasitic infection may be but is not limited to, amebiasis, Echinococcus infections, Fascioliasis, Hymenolepsis infection, Leishmaniasis, Onchocerciasis, Necator americanus infection, neurocysticercosis, Paragonimiasis, Plasmodium infections, Pneumocystis infection, Schistosomiasis, Taenia infection, Trichomonas vaginalis infection, Trichuris trichuria infection, Trypanosoma brucei infection and Trypanosoma cruzi infection. Parasites include Plasmodium spp. such as Plasmodium falciparum, Plasmodium malariae, Plasmodium ovale, and Plasmodium vivax and Toxoplasma gondii. Blood-borne and/or tissues parasites include Plasmodium spp., Babesia microti, Babesia divergens, Leishmania tropica, Leishmania spp., Leishmania braziliensis, Leishmania donovani, Trypanosoma gambiense and Trypanosoma rhodesiense (African sleeping sickness), Trypanosoma cruzi (Chagas' disease), and Toxoplasma gondii.

Other medically relevant microorganisms have been described extensively in the literature, e.g., see C. G. A Thomas, Medical Microbiology, Bailliere Tindall, Great Britain 1983, the entire contents of which is hereby incorporated by reference.

The methods of the invention are useful for treating a subject that has, or is at risk of developing cancer. A subject at risk of developing a cancer is one who has a higher than normal probability of developing cancer (i.e., higher than the probability in the general population). These subjects include, for instance, subjects having a genetic abnormality, the presence of which has been demonstrated to have a correlative relation to a higher than normal likelihood of developing a cancer and subjects exposed to cancer causing agents such as tobacco, asbestos, or other chemical toxins, or a subject who has previously been treated for cancer that is in apparent remission.

Exemplary cancers include, but are not limited to carcinomas or sarcomas. For example, the cancer may be basal cell carcinoma, biliary tract cancer, bladder cancer, bone cancer, brain cancer, breast cancer, cervical cancer, choriocarcinoma, CNS cancer, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, acute lymphoid leukemia, acute myeloid leukemia, chronic lymphoid leukemia, chronic myeloid leukemia, cutaneous T-cell leukemia, hairy cell leukemia, liver cancer, non-small cell lung cancer, small cell lung cancer, lymphoma, follicular lymphoma, Hodgkin's lymphoma, Non-Hodgkin's lymphoma, melanoma, myeloma, multiple myeloma, neuroblastoma, oral cavity cancer, ovarian cancer, pancreatic cancer, prostate cancer, rectal cancer, renal cancer, cancer of the respiratory system, retinoblastoma, rhabdomyosarcoma, skin cancer, squamous cell carcinoma, stomach cancer, testicular cancer, thyroid cancer, cancer of the urinary system and uterine cancer.

The invention can also be used to treat cancer and tumors in non human subjects. Cancer is one of the leading causes of death in companion animals (i.e., cats and dogs). Cancer usually strikes older animals which, in the case of house pets, have become integrated into the family. Forty-five % of dogs older than 10 years of age, are likely to succumb to the disease. The most common treatment options include surgery, chemotherapy and radiation therapy. Others treatment modalities which have been used with some success are laser therapy, cryotherapy, hyperthermia and immunotherapy. The choice of treatment depends on type of cancer and degree of dissemination. Unless the malignant growth is confined to a discrete area in the body, it is difficult to remove only malignant tissue without also affecting normal cells.

Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma. Other neoplasias in dogs include genital squamous cell carcinoma, transmissable veneral tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an evermore popular house pet is known to develop insulinoma, lymphoma, sarcoma, neuroma, pancreatic islet cell tumor, gastric MALT lymphoma and gastric adenocarcinoma.

Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium Corynebacterium pseudotuberculosis, and contagious lung tumor of sheep caused by jaagsiekte.

In any of the methods as described herein the subjects may be further administered other therapeutic agents or regimens. Examples include anti-microbial agents, anti-cancer agents, anti-allergy agents and anti-asthma agents. These other agents may be formulated together with or separately from immunogenic compositions of the invention.

Also included in the invention are methods for treating or preventing an allergic response comprising administering to a subject at risk of developing an allergic response an immunostimulatory composition comprising a combination of two or more Toll Like Receptor (TLR) agonists, each in an amount that in combination with the other induces an immune response, and wherein the immunostimulatory composition is administered in an amount effective to treat or prevent the allergic response.

In certain embodiments of the method, the immunostimulatory composition further comprises an antigen, and the allergic response is directed to the antigen.

Also included in the invention are methods for treating or preventing an autoimmune response in a subject comprising administering to a subject in need thereof an effective amount of an immunostimulatory composition comprising a combination of two or more Toll Like Receptor (TLR) agonists, each in an amount that in combination with the other prevents an autoimmune response.

In certain embodiments of the method, the immunostimulatory composition further comprises an antigen, and the allergic response is directed to the antigen.

Also included in the invention are methods for treating or preventing a symptom of an autoimmune disease comprising administering to a subject at risk of developing an autoimmune disease an effective amount of an immunostimulatory composition comprising a combination of two or more Toll Like Receptor (TLR) agonists, each in an amount that in combination with the other suppresses an autoimmune response, and an antigen, wherein said autoimmune disease involves an immune response to the antigen, and wherein the immunostimulatory composition is administered in an amount effective to treat or prevent a symptom of the autoimmune disease.

In the methods as described herein, at least one TLR agonist is a TLR3 agonist.

In certain embodiments of the methods as described herein, each of the TLR agonists alone does not induce an immune response.

Pharmaceutical Compositions

Also included in the invention are pharmaceutical compositions comprising a combination of two or more Toll Like Receptor (TLR) agonists with a carrier. The pharmaceutical compositions can comprise a combination of two or more Toll Like Receptor (TLR) agonists with a carrier, wherein at least one TLR agonist is a TLR3 agonist. The pharmaceutical compositions can comprise a combination of two or more Toll Like Receptor (TLR) agonists with a carrier, wherein at least one TLR agonist is a TLR3 agonist, and at least another TLR agonist is a TLR2 agonist. The pharmaceutical compositions can comprise a combination of two or more Toll Like Receptor (TLR) agonists with a carrier, wherein at least one TLR agonist is a TLR3 agonist, and at least another TLR agonist is a TLR9 agonist. The pharmaceutical compositions can comprise a combination of three or more Toll Like Receptor (TLR) agonists with a carrier, wherein at least one TLR agonist is a TLR3 agonist, at least another TLR agonist is a TLR2 agonist, and at least another TLR agonist is a TLR9 agonist.

The pharmaceutical compositions as described herein, in exemplary embodiments, induce an immune response. Each TLR agonist alone induces limited or no immune response. For example, low doses of each TLR agonist are used at which each TLR agonist alone induces a limited or no IR.

In certain exemplary embodiments, the pharmaceutical composition further comprises one or more antigens. The pharmaceutical compositions that comprise an antigen can be delivered in an antigen delivery system, for example a peptide, protein, plasmid DNA, live microbial vector, or attenuated microbial vector.

Administration

The pharmaceutical compositions of the invention, including TLR agonist combinations as described herein, and including TLR agonist combination that further comprise an antigen, are used in the preparation of medicaments, for treating the conditions described herein. These compositions of the invention are administered as pharmaceutically acceptable compositions. The pharmaceutical compositions as described herein can be administered in combination with other pharmaceutical and/or immunostimulatory agents, as described herein, and can be combined with a physiologically acceptable carrier. The compositions may be administered by any suitable means, including, but not limited to, intravenously, parenterally or locally. The compositions can be administered in a single dose by bolus injection or continuous infusion or in several doses over selected time intervals in order to titrate the dose.

In some embodiments, the pharmaceutical compositions are administered in conjunction with a composition comprising an antigen. The composition can also comprise and an adjuvant or other immunostimulatory agent. For example, the pharmaceutical compositions are administered with an emulsion of antigen and an adjuvant.

In some embodiments, the pharmaceutical compositions of the invention, including TLR agonist combinations as described herein, and including TLR agonist combination that further comprise one or more antigens, are used in the preparation of microcarriers or nanoparticles.

The term "microcarrier" refers to a particulate composition which is insoluble in water and which has a size of less than about 100 µm preferably less than about 50-60 µm, preferably less than about 10 µm, preferably less than about 5 µm. Microcarriers include "nanocarriers", which are microcarriers have a size of less than about 1 µm, preferably less than about 500 nm. Microcarriers include solid phase particles such a particles formed from biocompatible naturally occurring polymers, synthetic polymers or synthetic copolymers, including agarose or cross-linked agarose. Solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, dextran, and ferromagnetic and paramagnetic materials. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, phospholipid and adjuvant-active saponin) without antigen, or droplets or micelles found in oil-in-water or water-in-oil emulsions. Biodegradable liquid phase microcarriers typically incorporate a biodegradable oil, a number of which are known in the art, including squalene and vegetable oils. Microcarriers are typically spherical in shape, but microcarriers which deviate from speherical shape are also acceptable (e.g., ellipsoidal, rod-shaped, etc.). Due to their insoluble nature, microcarriers are filterable from water and water-based (aqueous) solutions.

Examples of nanoparticles include, but are not limited to, nanocrystalline particles, nanoparticles made by the polymerization of alkylcyanoacrylates and nanoparticles made by the polymerization of methylidene malonate. Additional surfaces to which antigens may be adsorbed include, but are not limited to, activated carbon particles and protein-ceramic nanoplates.

Adsorption of polypeptides to a surface for the purpose of delivery of the adsorbed molecules to cells is well known in the art. See, for example, Douglas et al. (1987) Crit. Rev. Ther. Drug. Carrier Syst. 3:233-261; Hagiwara et al. (1987) In Vivo 1:241-252; Bousquet et al. (1999) Pharm. Res. 16:141-147. Preferably, the material comprising the adsorbent surface is biodegradable. Adsorption of antigens to a surface may occur through non-covalent interactions, including ionic and/or hydrophobic interactions.

In general, characteristics of nanoparticles, such as surface charge, particle size and molecular weight, depend upon polymerization conditions, monomer concentration and the presence of stabilizers during the polymerization process (Douglas et al., 1987, Supra). For example, antigens of negative charge can adsorb directly to cationic surfaces of a microparticle. The surface of carrier particles may be modified, for example, with a surface coating, to allow or enhance adsorption of the antigens. Carrier particles with adsorbed antigens may be further coated with other substances. The addition of such other substances may, for example, prolong the half-life of the particles once administered to the subject and/or may target the particles to a specific cell type or tissue, as described herein.

Nanocrystalline surfaces to which antigens may be adsorbed have been described. Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987, Supra). Another adsorbent surface are nanoparticles made by the polymerization of methylidene malonate. For example, as described in Bousquet et al., 1999, Supra, polypeptides adsorbed to poly(methylidene malonate 2.1.2) nanoparticles appear to do so initially through electrostatic forces followed by stabilization through hydrophobic forces.

As used herein, "pharmaceutically acceptable excipient" includes any material which, when combined with an active ingredient of a composition, allows the ingredient to retain biological activity without causing disruptive reactions with the subject's immune system. Various pharmaceutically acceptable excipients are well known in the art.

Exemplary pharmaceutically acceptable excipients include sterile aqueous or non-aqueous solutions and suspensions. Examples include, but are not limited to, any of the standard pharmaceutical excipients such as a phosphate buffered saline solution, water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Compositions comprising such excipients are formulated by well known conventional methods (see: for example, Remington's Pharmaceutical Sciences, 18th Ed., Mack Publishing Co.).

As with all immunogenic compositions, the immunologically effective amounts and method of administration of the particular pharmaceutical composition can vary based on the individual, what condition is to be treated and other factors evident to one skilled in the art. Factors to be considered include the stage and severity of disease being treated, route of administration and the number of doses to be administered, the weight and general health of the recipient individual and the judgement of the prescribing physician. Such factors are known in the art and it is well within the skill of those in the art to make such determinations without undue experimentation. An "effective amount" or a "sufficient amount" of a substance is that amount sufficient to effect beneficial or desired results, including clinical results, and, as such, an "effective amount" depends upon the context in which it is being applied. An effective amount can be administered in one or more administrations.

A suitable dosage range is one that provides the desired modulation of immune response. Generally, dosage is determined by the amount of pharmaceutical composition administered to the patient, rather than the overall quantity of pharmaceutical composition. Useful dosage ranges of the pharmaceutical composition may be, for example, from about any of the following: 0.01 µg to 1000 µg per dose, 0.1 µg to 100 µg per dose, and 1.0 µg to 10 µg per dose. Generally, dosage ranges for initial immunization (that is for therapeutic or prophylactic administration) are from about any of the following: 1.0 µg to 100 µg per dose, 1.0 µg to 50 µg per dose, 1.0 µg to 10 µg per dose, followed by boosting dosages of from about any of the following: 1.0 µg to 100 µg per dose, 1.0 µg to 50 µg per dose, 1.0 µg to 10 µg per dose per dose, pursuant a boosting regimen over weeks to months depending upon the individual's response and condition by measuring, for example, CTL activity of cells circulating in the individual. Suitable volumes for parenteral administration are about 0.1 to 1.0 ml per injection site. The absolute amount given to each patient depends on pharmacological properties such as bioavailability, clearance rate and route of administration.

For the administration of ex vivo treated cells, typically, about 10.sup.6-10.sup.10 cells can be administered in a volume of 50 .µlto 1 liter, 1 ml to 1 liter, 10 ml to 250 ml, 50 ml to 150, and typically 100 ml. The volume will depend upon, for example, the type of cell administered, the disorder treated and the route of administration.

Single or multiple administrations of the compositions and/or cells can be carried out with dose levels and pattern being selected by the treating physician.

The effective amount and method of administration of the particular pharmaceutical composition can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. The absolute amount given to each patient depends on pharmacological properties such as bioavailability, clearance rate and route of administration.

Parenteral routes of administration include but are not limited to electrical (iontophoresis) or direct injection such as direct injection into a central venous line, intravenous, intramuscular, intraperitoneal, intradermal, or subcutaneous injection. Pharmaceutical formulations suitable for parenteral administration are generally formulated in USP water or water for injection and may further comprise pH buffers, salts bulking agents, preservatives, and other pharmaceutically acceptable excipients. Formulations for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations suitable for administration by inhalation including, but not limited to, liquid suspensions for forming aerosols as well as powder forms for dry powder inhalation delivery systems. Devices suitable for administration by inhalation of antigen-scaffold complex formulations include, but are not limited to, atomizers, vaporizers, nebulizers, and dry powder inhalation delivery devices.

Analysis (both qualitative and quantitative) of the immune response to the pharmaceutical compositions comprising a combination of two or more Toll Like Receptor (TLR) agonists, or to the cells treated with the pharmaceutical compositions can be by any method known in the art, including, but not limited to, measuring activation of specific populations of lymphocytes such as CD4+ T cells or CD8+ CTLs, production of cytokines such as IFN-.gamma, IFN-alpha, IL-2, IL-4, IL-5, IL-10 or IL-12 and/or antigen-specific antibody production (including measuring specific antibody subclasses). Measurement of a T cell proliferative response can be performed for instance through measuring BrdU incorporation as known in the art. Measurement of numbers of specific types of lymphocytes such as CD4+ T cells can be achieved, for example, with fluorescence-activated cell sorting (FACS). Cytotoxicity and CTL assays, such as chromium release assays, can be performed as known in the art. Cytokine concentrations can be measured, for example, by ELISA. Methods for measuring specific antibody responses include enzyme-linked immunosorbent assays (ELISA and ELISPOT) and are well known in the art. These and other assays to evaluate the immune response to an immunogen are well known in the art. See, for example, Current Protocols in Immunology (1991, Coligan et al., eds.).

The term "co-administration" as used herein refers to the administration of at least two different substances sufficiently close in time to modulate an immune response. Co-administration can refer to simultaneous administration of at least two different substances.

Kits

Included in the invention are kits comprising the immunostimulatory compositions of the invention as described herein. In certain embodiments, the kits can comprise an immunostimulatory composition comprising a combination of two or more Toll Like Receptor (TLR) agonists, as described herein, each in an amount that in combination with the other induces an immune response, and instructions for use. The kits can further comprise one or more antigens, as described herein, and instructions for use.

The instructions relating to the use of the immunostimulatory composition generally include information as to dosage, dosing schedule, and route of administration for the intended treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

It should be appreciated that the invention should not be construed to be limited to the examples that are now described; rather, the invention should be construed to include any and all applications provided herein and all equivalent variations within the skill of the ordinary artisan.

A host relies on an immune mechanism that is sensitive enough to effectively defend against microbial invasion, and immune responses may be initiated due to the interplay between different TLRs upon concurrent stimulation even in small amounts. Accordingly, TLRs play a critical role for the host to generate cellular immunity against invading microorganisms. Each TLR is specific for a certain range of microbial components, and more than one is likely to be involved in any natural infection. As reported herein, certain TLRs can act synergistically in response to microbial stimuli in specific, non-random, combinations. As reported herein, vaccination of mice with antigenic peptide together with pairs of ligands for TLR2 and 3 or 3 and 9 effectively primed T cells in vivo, while each individual ligand or paired TLR2 and 9 ligands at the same doses were ineffective. Dendritic cells (DCs) appeared to play a central role in response to the synergistic combinations of TLR ligands by amplifying production of inflammatory cytokines and chemokines, such as IL-12, TNF-alpha and RANTES, through MyD88-dependent signaling pathway. Costimulatory molecules such as, but not limited to, CD86 were upregulated by TLR3 ligand alone but not further increased when either TLR2 or 9 ligand was added. Also, no synergy was observed between TLR2 and 9 ligands in DC activation. Accordinglt, the experiments demonstrate a nonrandom, synergistic TLR interplay pattern in which triggering of TLR3 together with TLR2 and/or 9, but not the combination of TLR2 and 9, at suboptimal doses for each, synergistically activates DCs and leads to immediate induction of T cell responses.

Moreover, even more potent immune responses were observed when all three types of TLR ligands were administered together.

The results presented herein suggest a strategic use of TLRs in host defense mechanisms, and have important implications in the design of vaccine adjuvants.

Example 1

TLR Ligands Prime CD8+ T Cell in Synergistic, Nonrandom Manner

In a first set of experiments, to examine the role of TLRs in combinations in vivo and their specific synergy patterns, macrophage activating lipoprotein (MALP)-2 (for TLR 2/6), PolyI:C (for TLR3) and CpG Oligodeoxynucleotide (ODN) (for TLR9) at suboptimal doses (see Methods) were used for a systematic study of TLR synergistic interplay both in vivo in mice and in vitro using mouse cells. First, BALB/c mice were immunized (H-2Dd) subcutaneously by footpad injection with PCLUS3-18IIIB, an antigenic HIV peptide containing the H-2Dd-restricted CTL epitope P18I10 linked to a T-helper peptide (PCLUS3) (34), together with paired TLR ligands, and examined T cell priming in the draining (popliteal) lymph nodes (LNs) by flow cytometry using P18I10 tetramers. At the suboptimal doses at which each single ligand did not induce significant responses, MALP-2+PolyI:C and PolyI:C+CpG combinations effectively primed antigen-specific T cells in a synergistic way, as assayed at day 5 after immunization (FIG. 1A). Over the entire priming phase in the draining LNs, the numbers of antigen-specific and functional CD8+ T cells were synergistically induced as shown by MALP-2+PolyI:C (FIG. 1B-D). However, in contrast, the MALP-2+CpG combination was found ineffective (FIG. 1A). Thus, the results imply a functional, nonrandom interplay of different TLRs in priming naïve T cells.

Example 2

DCs are Essential for the Specific TLR Combinations to Activate T Cells

TLRs are expressed by various cells including DCs, lymphocytes, mucosal epithelial cells, and macrophages (8, 9). In order to determine which cells were responsible for the T cell priming, an initial investigation into the mechanism of the observed specific TLR synergistic interplay was carried out.

Figure 2:
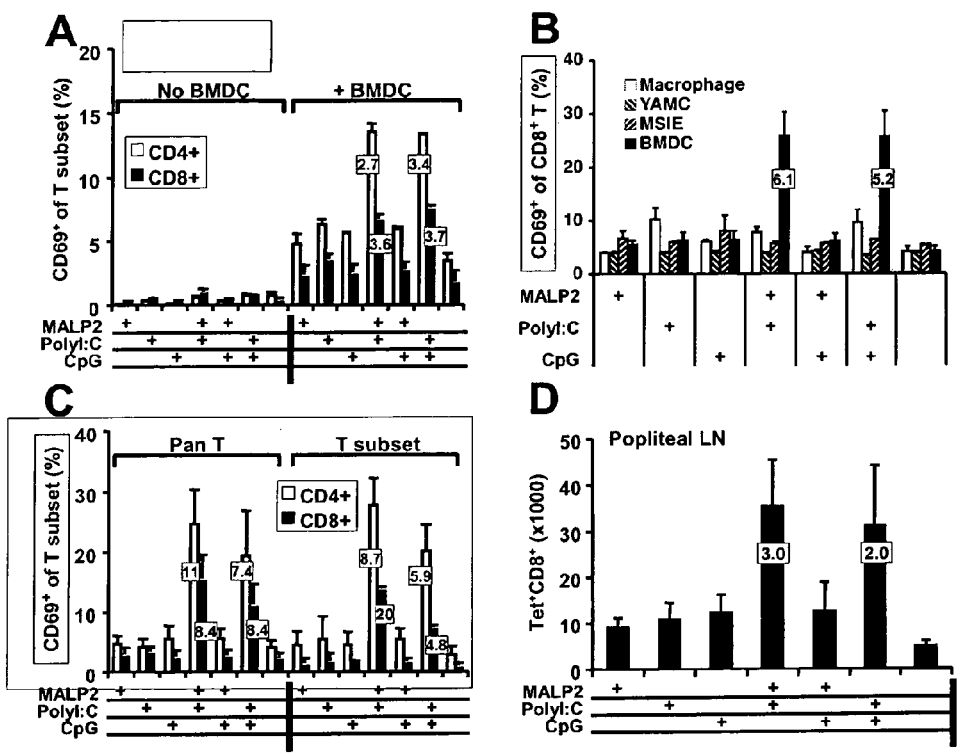
FIGS. 2(A-D) shows that TLR ligands activate T cells through synergistic activation of DCs. Mouse bone marrow derived DCs (BMDCs) were stimulated with TLR ligands, MALP-2, Poly I: C and CpG singly or pairwise, for 20 hours and excess ligands were washed off before coculture with T cells or immunization. Panel (A) is a graph showing CD69 expression on gated subsets of total T cells assayed by flow cytometry after 24-hour in vitro stimulation with TLR ligands (No BMDC) or cultured with TLR ligand-pretreated DCs (+BMDC). Panel (B) is a graph showing CD69 expression after 24 hours of coculture with stimulator cells (YAMC: young adult mouse colon epithelial cells; MSIE: mouse small intestinal epithelial cells). The stimulator cells were pretreated with TLR ligands for 20 hours before the coculture. Panel (C) is a graph showing CD69 expression on separated CD4+ and CD8+ T cells after 20 hours of in vitro coculture with DCs. Panel (D) is a graph showing the total number of tet+CD8+ T cells in the popliteal LNs 5 days after immunization with DCs pretreated with TLR ligands and pulsed with P18I10 peptide.

First, purified total T cells freshly isolated from naïve mouse spleens in vitro were stimulated with single and pairwise combinations of TLR ligands (MALP-2, PolyI:C, and CpG) for 24 hrs. Direct stimulation of TLRs without antigen-presenting cells did not induce T cells to express CD69 (FIG. 2A). Neither intestinal epithelial cells (of large or small intestine) nor macrophages as nonprofessional antigen presenting cells manifested the synergy on T cells after TLR ligand stimulation (FIG. 2B). However, bone marrow derived DCs (BMDCs) pretreated with TLR ligands in the synergistic combinations, i.e. MALP-2+PolyI:C and PolyI:C+CpG, observed above induced CD69+ in T cells (FIG. 2A), in line with the in vivo results shown in FIG. 1. Simply doubling the dose of any one of these TLR ligands did not produce this enhanced response.

It is worth noting that both CD4+ and CD8+ T cells could be activated independently by DCs when stimulated as separated purified preparations (FIG. 2C), indicating that the response of each gated subset in the total T cell preparation (FIG. 2A) was not simply a bystander response from one to the other. Similar to the in vivo observation, MALP-2+CpG together were not effective at inducing synergy (FIG. 2A). These results suggest that DCs, as professional antigen-presenting cells, are most sensitive in recognizing TLR combinations, which may be a prerequisite for optimal TLR-initiated T cell responses.

To extend these observations to the effect of DCs following TLR treatment on T cell activation in vivo, TLR ligand-pretreated DCs were pulsed with peptide P18I10 and injected subcutaneously into the footpads of naïve mice. In the popliteal LNs (assayed at day 5), P18I10-specific CD8+ T cells were effectively induced by PolyI:C+MALP-2 or PolyI:C+CpG-pretreated DCs as opposed to DCs pretreated with single ligands or the non-synergistic MALP-2+CpG (FIG. 2D), indicating that the specific TLR synergy pattern observed in DC-mediated T cell activation in vitro corresponds with that in vivo. This also suggests that the in vivo T cell priming following immunization using TLR ligands, as shown in FIG. 1, is likely due to the effect of the TLR ligands on DCs.

Example 3

Synergistic TLRs Amplify MyD88-dependent Cytokines/Chemokines from DCs

Figure 3:
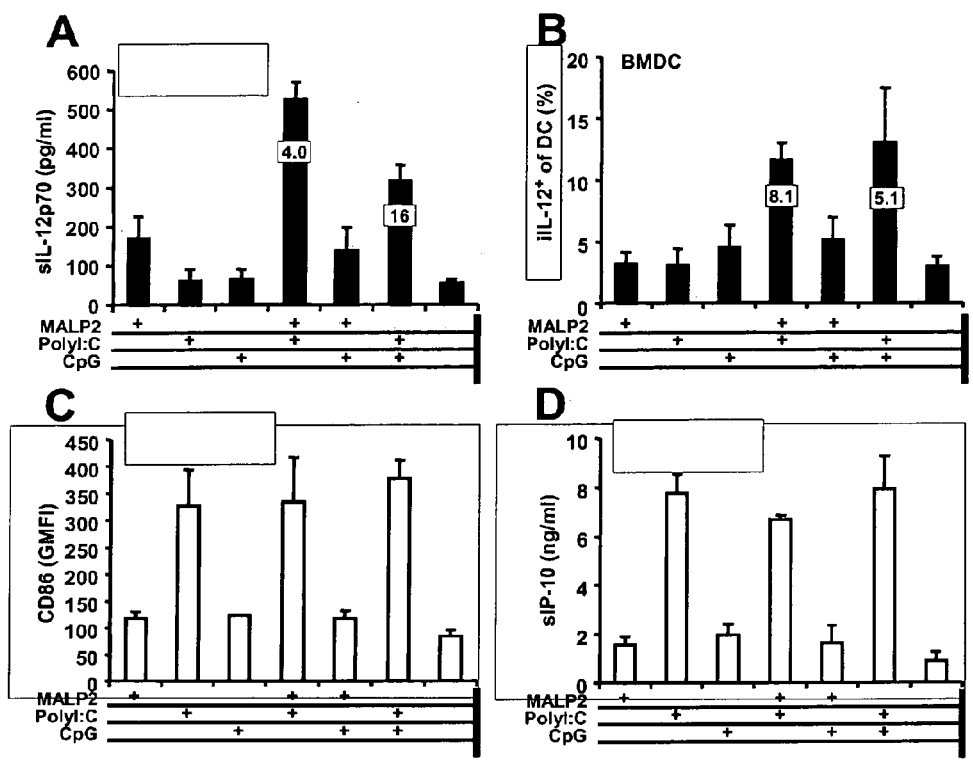
FIGS. 3(A-D) shows combinations of TLR ligands synergistically activate DCs in the amplification of MyD88-dependent cytokines/chemokines. BMDCs were stimulated in vitro with TLR ligands as indicated for 20 hours. Secreted IL-12p70 (sIL-12p70), shown in the graph in panel (A), and sIP-10, shown in the graph in panel (D), were measured in the supernatants with a multiplex cytokine system. Percent of intracellular IL-12+ (iIL-12+) cells out of DCs is shown in the graph in panel (B) and surface expression of CD86 expressed as geometric mean fluorescence intensity (GMFI) shown in the graph in panel (C) were analyzed by flow cytometry based on gated MHC class II+CD11c+ DCs.
Figure 8:
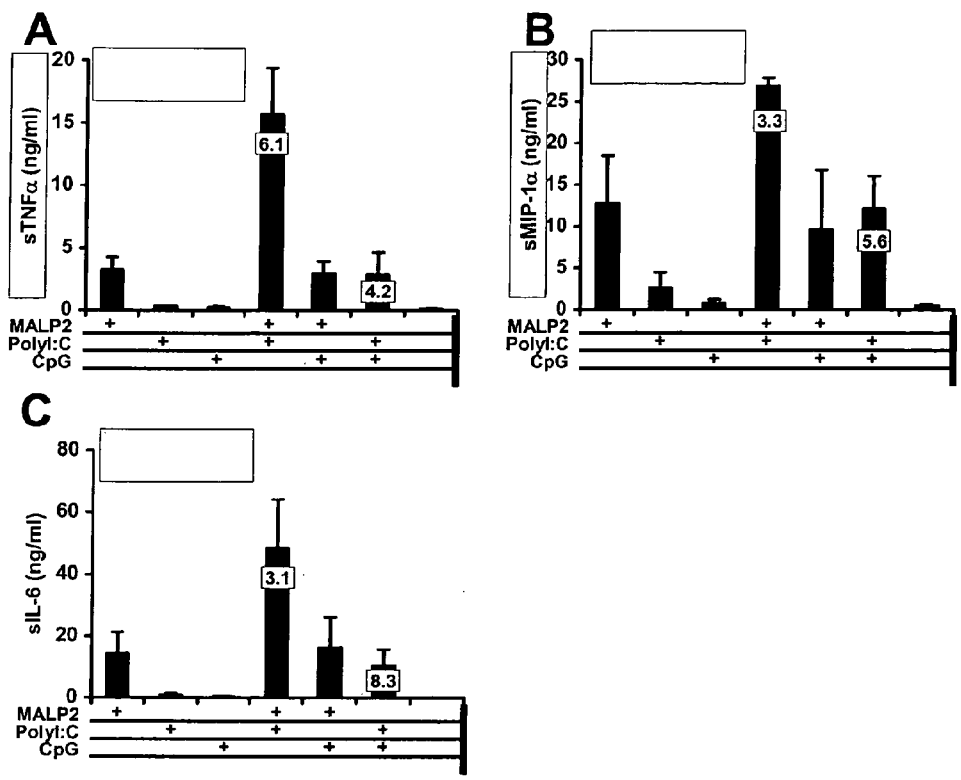
FIGS. 8(A-C) shows cytokines and chemokines secreted by DC. BMDCs were pretreated with TLR ligands, MALP-2, PolyI:C and CpG ODN. After 20 hours, sTNFa in panel (A), sMIP-1a in panel (B) and sIL-6 in panel (C) in the supernatants (assayed with a multiplex cytokine system), as well as iIL-12+ DCs in panel (D), measured by flow cytometry. Value on bars (as in other figures) indicates a synergy between two ligands.

Since the above results indicate that the synergistic T cell response depends on the nonrandom interplay of TLRs on DCs, it was next explored whether it is due to a nonrandom synergistic activation of DC. Treatment of BMDCs in vitro with either MALP-2+PolyI:C or PolyI:C+CpG resulted in synergistically increased secretion of IL-12p70 (sIL-12) assayed in the culture in the supernatants (FIG. 3A). Intracellular cytokine staining showed an increased number of DCs producing IL-12p70/40 (iIL-12+) (FIG. 3B), in agreement with the secreted (s)IL-12. sTNFa, sMIP-1a and sIL-6 (FIG. 8) in the supernatant were also elevated, albeit to a higher level by the former combination than the latter. LTA which, like MALP-2, uses TLR2/6 could also act synergistically with PolyI:C to boost IL-12 production, whereas strikingly PGN and PAM3CSK4 which use TLR2/1 could not (FIG. 9A), suggesting that the synergy depends on using the TLR2/6 combination with TLR3. In contrast, MALP-2+CpG did not increase IL-12 production as compared to single ligands (FIGS. 3A and 3B), suggesting a nonrandom synergistic TLR activation of DC.

Figure 9:
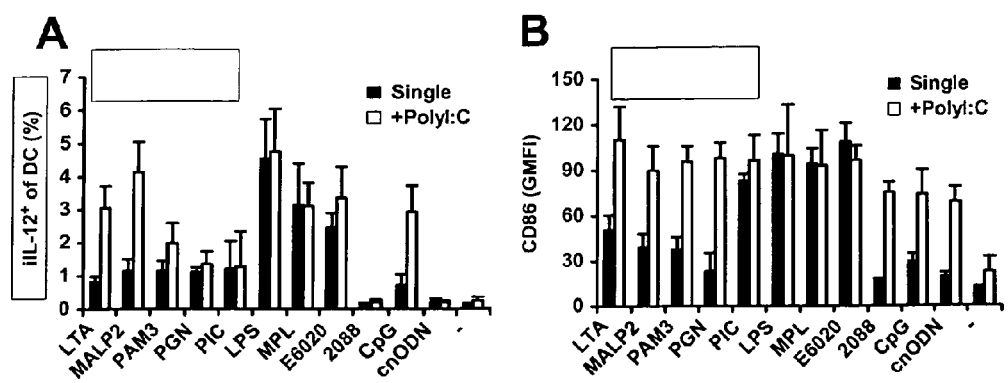
FIGS. 9(A and B) shows DC activation by TLR ligands. BMDCs were treated with various TLR ligands in addition to MALP-2, PolyI: C and CpG: LTA 25 mg/ml, PAM3CSK (PAM3) 0.3 mg/ml, LPS 1 mg/ml, MPL 0.01 mg/ml, E6020 10 mg/ml, suppressive ODN 2088 3 mg/ml, Control (Cntrl) ODN 3 mg/ml. After 20 hours, iIL-12+ DCs shown in panel (A) and CD86 expression shown in panel (B) were measured.

PolyI:C alone could activate DCs to upregulate CD86 expression and produce IP-10 (FIGS. 3C and 3D); however, addition of MALP-2 or CpG did not result in a further increase in these DC functions compared to PolyI:C alone (FIGS. 3C and 3D). Similarly, other TLR2 ligands did not show synergy with PolyI:C to enhance CD86 expression (FIG. 9B). Expression of CD86 and production of IP-10 induced through TLR3 did not seem to parallel T cell activation as well as did IL-12 and TNFa production seen above.

Figure 4:
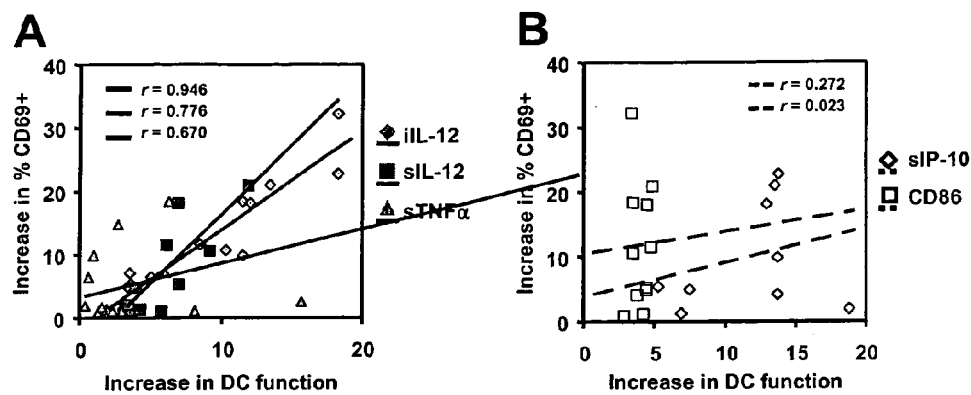
FIGS. 4(A and B) shows T cell activation is correlated with synergistic MyD88-dependent DC activation. Correlation between CD69-expressing responsive T cells and increases in MyD88-dependent (IL-12 and TNFa) (panel A) or MyD88-independent DC functions (CD86 and IP-10) (panel B) was plotted. Responsiveness of T cells was determined as more than two fold increases in percentage of CD69+ out of CD8+ T cells. One tenth of original values on increases in soluble TNF alpha (sTNFa) are shown in order to fit in the same scale with the others.

It has been suggested that TLR signaling involves MyD88-dependent or MyD88-independent, TRIF-dependent pathways for activation of targeted cells to produce various inflammatory molecules (3, 35, 36). To quantitatively compare the effect of DC functions on T cell activation, we estimated Pearson's correlation coefficient (r) between functioning DCs and T cells expressing CD69. Surprisingly, the increase in activated T cells (CD69+CD8+) was strongly correlated with elevated MyD88-dependent cytokines sIL-12 ($r=0.776$, $p=0.005$) and sTNFa ($r=0.670$, $p=0.003$) from DCs (FIG. 4A). A stronger correlation was seen with the increase in number of iIL-12+ DCs ($r=0.945$, $p=0.0001$) (FIG. 4A). In contrast, T cell activation was poorly correlated with TRIF-dependent MyD88-independent production of IP-10 ($r=0.272$, $p=0.476$) and CD86 expression ($r=0.023$, $p=0.948$) by DCs (FIG. 4B). One implication is that amplification of MyD88-dependent cytokines/chemokines contributes to the synergy in T cell activation. Overall, the combinatorial activity of TLRs in T cell priming may be due to the nonrandom, synergistic activation of DCs.

Figure 5:
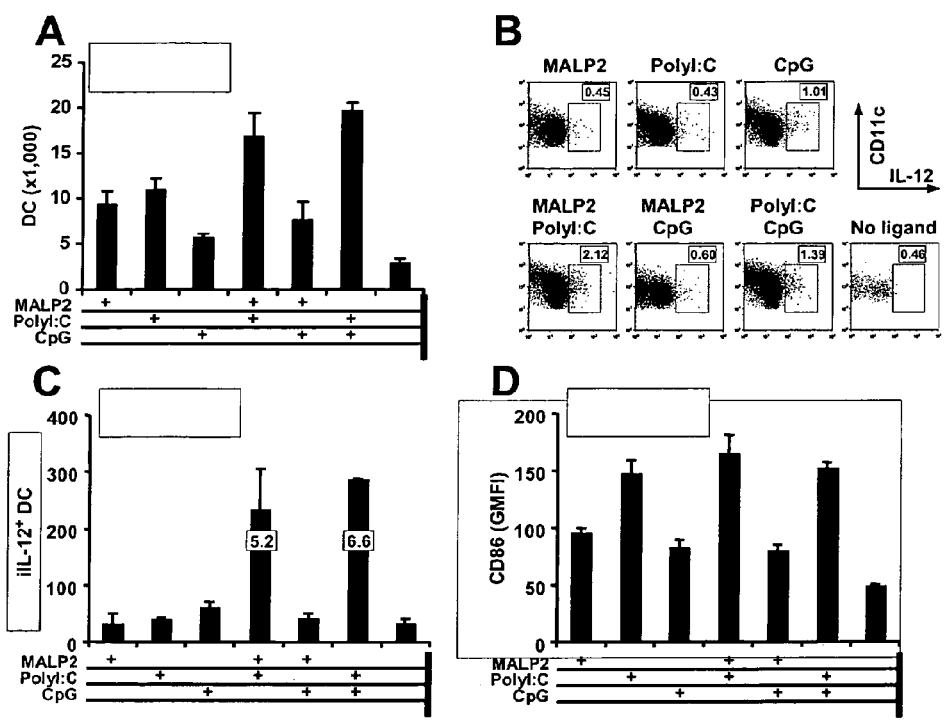
FIGS. 5(A-D) shows TLR ligands synergistically activate DCs in vivo. Mice were immunized in the footpads with MALP-2, PolyI:C and CpG singly or pairwise. Paired popliteal LN cells were isolated 36 hours later for assay by flow cytometry. Panel (A) is a graph showing the total numbers of popliteal LN MHC class II+CD11c+ DCs from paired popliteal LNs. Panel (B) shows representative flow cytometry staining showing percent of iIL-12+ cells out of MHC class II+CD11c+ DCs. Panel (C) is a graph showing the total numbers of iIL-12+MHC class II+CD11c+ DCs. Panel (D) is a graph showing CD86 expression on DCs.

If this hypothesis were true, it may be expected that use of synergistic combinations of TLRs as adjuvant would result in similar activation of DCs in vivo. To test this hypothesis, DCs were isolated from popliteal LNs following footpad immunization with TLR ligands and examined ex vivo. Compared to single ligands and the MALP-2+CpG, administration of the synergistic TLR combinations MALP-2+PolyI:C and PolyI:C+CpG increased total numbers of DCs, although not significantly synergistic, in the popliteal LNs at 36 hours after immunization (FIG. 5A). However, total numbers of functioning DCs as assayed by ex vivo intracellular staining of IL-12 were significantly increased ($P<0.01$) (FIGS. 5B and 5C). Expression of CD86 by LN DCs was found to be upregulated by PolyI:C alone and no significant increases were observed when either MALP-2 or CpG was included (FIG. 5D). These results are in line with the above in vitro observations. Therefore, the interplay of TLRs in activating DCs in vivo is nonrandom and mediated through potentiating MyD88-dependent cytokines that could account for the activation of specific T cells.

Thus, the data presented herein demonstrates that CD86 and IP-10 could be upregulated by stimulation of TLR3 alone, but this MyD88-independent DC activation/maturation was not augmented when TLR2 or 9 signaling through MyD88 was also stimulated, and did not correlate with T cell activation. Also, TLR2 and 9 did not synergize with each other to activate DCs or prime T cells. However, triggering of TLR3 significantly enhanced TLR2- or 9-mediated MyD88-dependent DC functions, and this strongly correlated with subsequent T cell activation. Thus, the host employs a unidirectional system for TLRs to synergize with each other inside cells.

It is worth noting that the number of IL-12-producing DCs showed a stronger correlation with T cell activation than secreted IL-12 levels, suggesting that the quantity of functional antigen-presenting cells may be more important in generating activated T cells than the total amount of cytokine secreted, since both types of cells need a close contact to interact. The unidirectional DC activation for T cell activation may be supportive of the previous postulation of DC-derived cytokines as "signal 3" (37, 38). Although signal 2 provided by, for example, CD86 through activation of the MyD88-independent pathway increases the likelihood of T cell priming, it is still not decisive of a T cell response (39, 40).

Example 4

TLR Synergy is Mediated Through the MyD88-cJun Signaling Pathway

Figure 6:
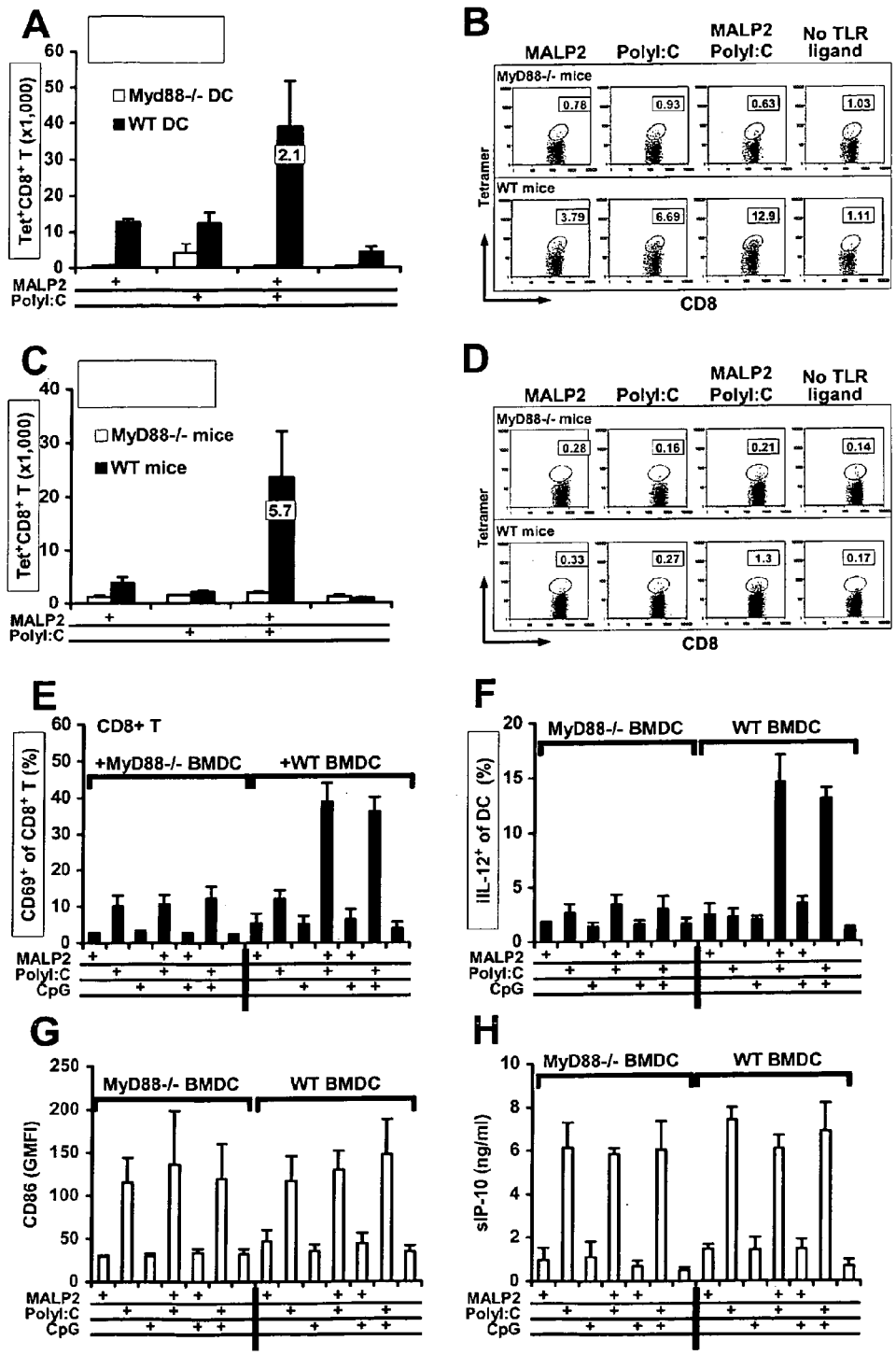
FIGS. 6(A-H) shows that synergistic activation of DC for T cell priming is MyD88-dependent. Panel (A) is a graph showing the total number of tet+CD8+ T cells in popliteal LNs of wild type mice at day 5 after immunization in the footpads with MyD88−/− or wild type DCs pretreated with TLR ligands and pulsed with SIINFEKL peptide. Panel (B) shows representative SIINFEKL tetramer stainings of LN CD8+ T cell 5 days after DC immunization. Panel (C) is a graph showing the total number of SIINFEKL tet+CD8+ T cells in popliteal LNs of MyD88−/− mice or wild type littermates at day 5 after footpad immunization with SIINFEKL peptide and TLR ligands. Panel (D) shows representative SIINFEKL tetramer stainings of LN CD8+ T cell 5 days after peptide immunization. Panel (E) shows the percent of CD69+CD8+ spleen T cells after 20 hours of coculture with MyD88−/− or WT DCs pretreated TLR ligands. MyD88−/− and wild type DCs were compared for producing intracellular IL-12 (iIL-12) in Panel (F). Panel (G) is a graph showing expression of surface CD86 after 20 hours of TLR stimulation. Panel (H) is a graph showing secretion of IP-10 after 20 hours of TLR stimulation.
Figure 10:
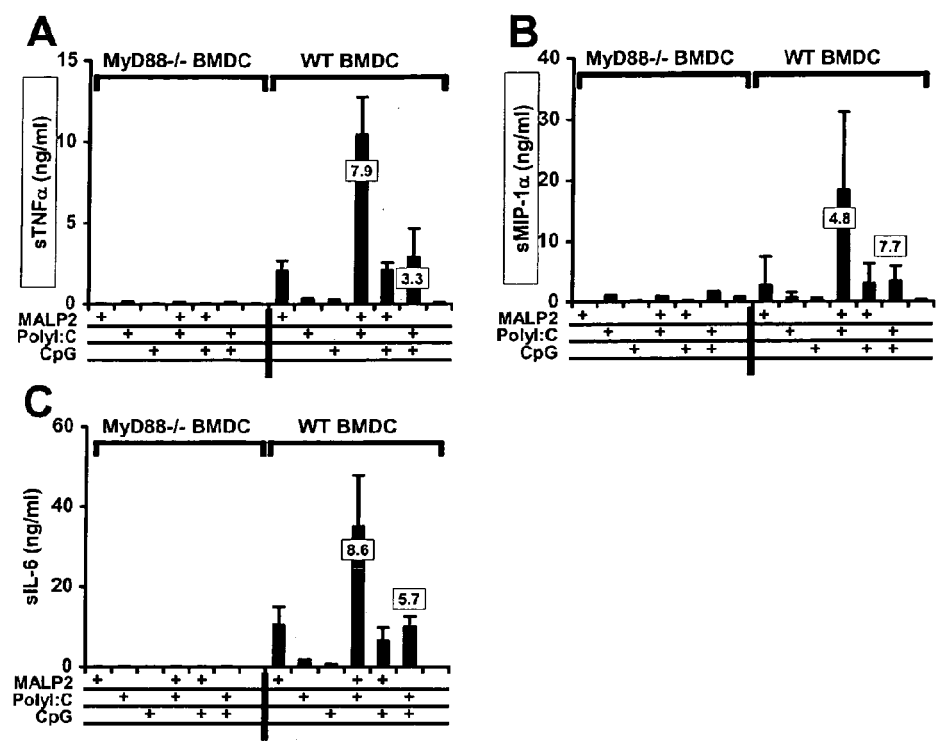
FIGS. 10(A-C) shows abolished cytokine production in MyD88−/− DCs. BMDCs isolated from MyD88−/− or wild type mice were treated with TLR ligands. STNFa, shown in the graph in panel (A), sMIP-1a, shown in the graph in panel (B) and sIL-6, shown in the graph in panel (C) were measured in the supernatants after 20 hours by a multiplex cytokine system.

It was next examined whether the MyD88 signaling pathway is indeed essential for T cell activation induced through combinatorial sets of TLRs. Mice were immunized with MyD88−/− or wild type BMDCs (both C57BL/6 H-2Kb background) pretreated with MALP-2+PolyI:C and pulsed with H-2Kb-restricted SIINFEKL peptide. SIINFEKL-specific CD8+ T cells in the popliteal LNs were examined 5 days after immunization. Animals immunized with MyD88−/− DCs with TLR stimulation did not develop significant tetramer positive CD8+ T cells, in contrast to those immunized with MALP-2+PolyI:C-pretreated wild type DCs (FIGS. 6A and 6B). When immunized with SIINFEKL peptide together with MALP-2+PolyI:C, mice deficient in MyD88 also failed to show enhanced antigen-specific T cell responses compared to wild type counterparts (FIGS. 6C and 6D). As opposed to wild type DCs, MyD88-deficient DCs pretreated with the synergistic TLR combinations failed to stimulate T cells to express CD69 (FIG. 6E). Further, production of MyD88-dependent cytokines IL-12 (FIG. 6F), TNFa, MIP-1a and IL-6 (FIG. 10) was diminished. In contrast, MyD88-independent upregulation of CD86 and IP-10 was barely affected in MyD88−/− DCs (FIGS. 6G and 6H). These results suggest that the synergistic TLR interplay on DC and subsequent T cell activation highly depend on the MyD88-dependent signaling pathway.

Figure 7:
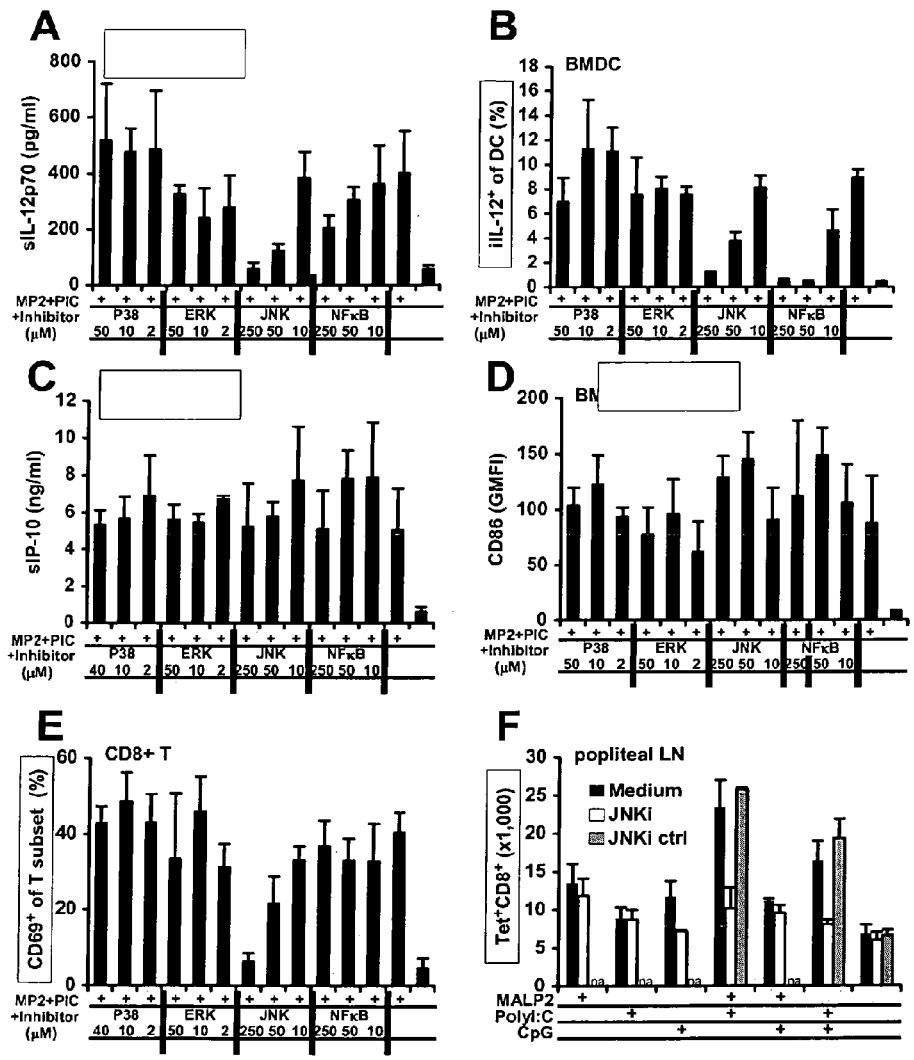
FIGS. 7(A-F) shows JNK is essential in the interplay of TLRs for synergistic DC-T cell activation. Inhibitors for P38, ERK, JNK or NF-kB at doses indicated (µM) were added to BMDC cultures 1 hour prior to the addition of TLR ligands. sIL-12p70 (panel A), iIL-12+ DCs (panel B) and sIP-10 (panel C) in the supernatants (assayed with a multiplex cytokine system), and CD86 expression (panel D) were measured after 20-hour stimulation with MALP-2+PolyI:C. Panel (E) shows the percent of CD69+CD8+ T cells after 24-hour coculture with DCs pretreated with MALP-2+PolyI:C in the presence of inhibitors. Panel (F) is a graph showing P18I10 tet+CD8+ T cells in popliteal LNs measured at day 5 after footpad immunization with DCs. Prior to immunization, DCs were treated with INK inhibitors followed by treatment with TLR ligands and pulsing with P18I10 peptide.
Figure 11:
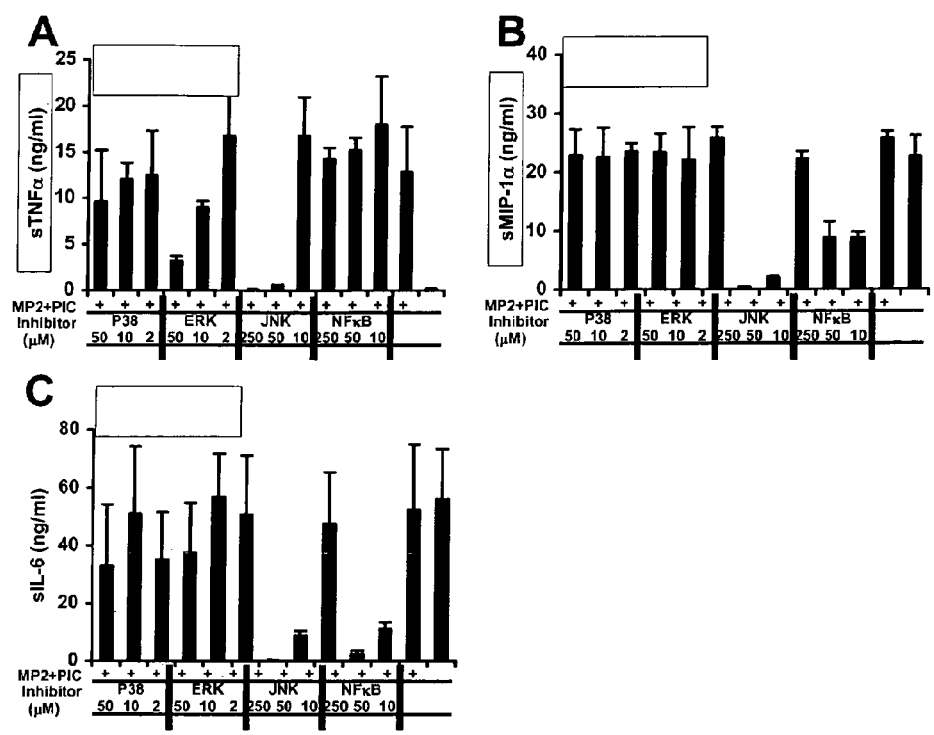
FIGS. 11(A-C) shows secretion of cytokines and chemokines by DC in the presence of MAPK and NF-kB inhibitors. BMDC were treated with the inhibitors for 1 hour prior to addition of TLR ligands. sTNFa shown in the graph in panel (A), sMIP-1a shown in the graph in panel (B) and sIL-6 shown in the graph in panel (C) in the supernatants were measured 20 hours later.

The MyD88-dependent signaling pathway is known to be primarily mediated through NF-kB and MAPKs (3, 23, 24). Following synergistic TLR triggering, both IL-12 secretion by wild type DCs (FIG. 7A) and the proportion of IL-12-producing DCs (FIG. 7B) were inhibited in the presence of NF-kB and JNK inhibitors. Production of TNFa, MIP-1a or IL-6 was also blocked by the JNK inhibitor and selectively by other inhibitors as well (FIG. 11). In contrast, none of these inhibitors blocked upregulation of CD86 and IP-10 (FIGS. 7C and 7D). However, the JNK inhibitor effectively blocked the DC function in T cell activation (FIG. 7E). To confirm the relevance of these findings in vivo, JNK inhibitor pretreated DCs were stimulated with the synergistic TLR combinations, pulsed with peptide P18I10, and then injected subcutaneously into mice. Further, these DCs were unable to efficiently prime antigen-specific T cells in the draining LNs in contrast to untreated DCs (FIG. 7F). Therefore, it appears that MyD88-dependent DC activation for T cell priming induced by the synergistic TLR combinations is mediated primarily through the JNK/c-Jun pathway.

Figure 12:
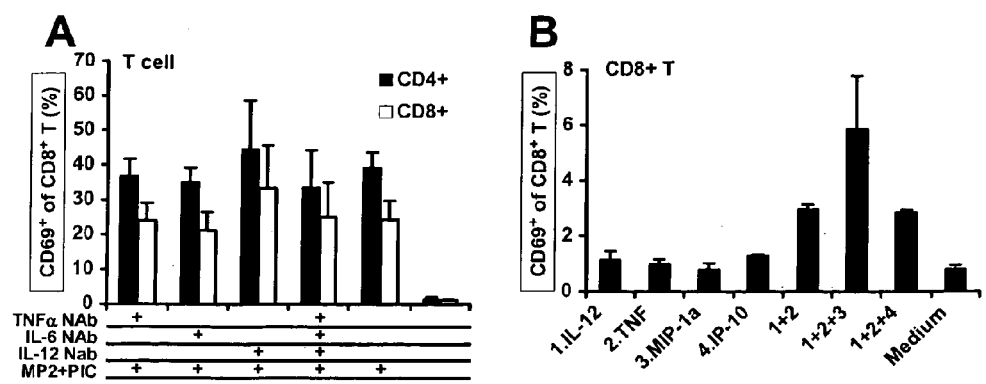
FIGS. 12(A and B) shows cytokine effects on T cell activation. Panel (A) is a graph showing the results when BMDC pretreated with MALP-2+PolyI:C were cultured with purified T cells in the presence of neutralizing antibodies against cytokines as indicated. CD69+ T cells were measured 24 hours later. Panel (B) is a graph showing the results when purified T cells were culture in the presence of IL-12 (25 ng/ml), TNFa (10 ng/ml), MIP-1a (50 ng/ml) and IP-10 (25 ng/ml) singly or in combinations as indicated. CD69+CD8+ T cells were measured after 24 hours of treatment.

As there are several MyD88-dependent inflammatory cytokines that are produced downstream of the JNK/c-Jun pathway, blocking one of these cytokines may not be expected to abolish the synergy effect. Accordingly, blockade of several known cytokines from activated DCs with neutralizing antibodies did not significantly attenuate the effect on T cell activation (FIG. 12A). Moreover, treatment with single recombinant MyD88-dependent cytokines/chemokines for 24 hours was not sufficient to stimulate naïve T cells to express substantial CD69, while multiple MyD88-dependent cytokines given simultaneously increased CD69 to a significant level (FIG. 12B). Adding IP-10, however, did not significantly enhance the response already induced by the MyD88-dependent cytokines (FIG. 12B). These results may suggest that multiple rather than single MyD88-dependent cytokines contribute to the synergy in T cell activation and that the synergistic effect of DCs on T cell activation may be generated presynaptically.

The data presented herein shows that JNK, as opposed to NF-kB and other MAPKs, is involved in signaling for the synergistic boosting of MyD88-dependent DC functions for T cell activation by the combination of TLR3 with TLR2 or 9. The engagement of JNK may be associated with differentiation of Th1 T cells (24), which may account for the increased number of antigen-specific CD8+ T cells seen in this study. Based on previous investigations that INK can be stimulated by PolyI:C (41, 42), it is possible that JNK may be an intracellular transduction point along the MyD88-dependent signaling pathway that is potentiated by the MyD88-independent pathway activated by TLR3.

If the combinatorial use of MyD88- and MyD88-independent signaling pathways exists, TLR4, which signals through both TRIF and MyD88 (10, 25, 36), would be capable of self-synergizing and acting similarly to TLR3 along with TLR2 and 9. Previous studies have shown that LPS responsiveness through TLR4 in cytokine production is abolished when either MyD88 or TRIF is deficient (10, 36, 43, 44). Indeed, LPS, MPL and E6020 alone showed an efficacy equivalent to PolyI:C in upregulation of CD86 expression, as well as to MALP-2+PolyI:C and PolyI:C+CpG in inducing IL-12 production from DCs (FIG. 9B). Addition of PolyI:C to the TLR4 stimulation did not further enhance IL-12 production (FIG. 9A), which explains the previous observation that triggering TLR3 does not synergize with TLR4 to induce greater effector functions (28, 30). Thus, the synergy mechanism described herein may possibly fit with what is known about TLR4-associated hypersensitivity immune response.

Example 5

Toll-Like Receptors (TLRs) Play an Important Role in Inducing Cellular Immunity

Figure 13:
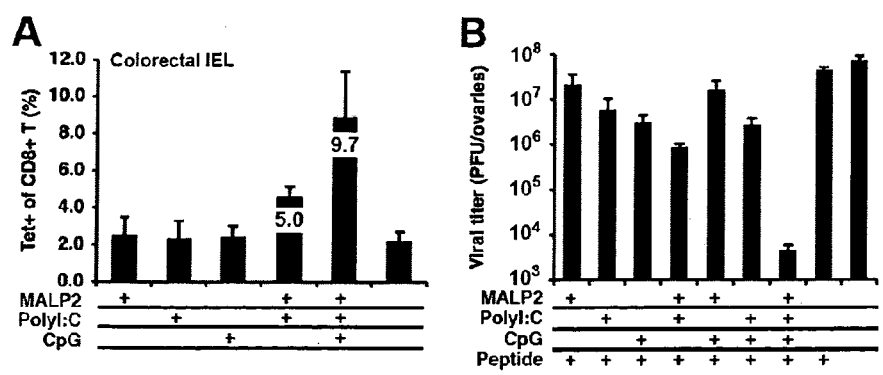
FIGS. 13(A and B) show TLR ligands act synergistically in inducing mucosal immunity. BALB/c mice were immunized intrarectally for 3 consecutive days with a mixture of PCLUS3-18IIIB containing the P18I10 epitope and TLR ligands (MALP-2, PolyI:C and CpG singly or pairwise or triply) formulated in DOTAP. In panel (A) colorectal intraepithelial lymphocytes (IEL) were isolated 3 months after immunization and stained with H-2Dd/P18I10 tetramers for flow cytometry to analyze antigen-specific CD8+ T cells. In the graph, the value on bars indicates the synergy between different ligands expressed as fold increase calculated by dividing the increase (subtracting the no ligand control) in the response to the paired ligands by the sum of that of the individual ligands. In panel (B) immunized mice were challenged intrarectally with vaccinia virus expressing antigen-containing P18I10. Viral titers were determined in paired ovaries removed 6 days after virus challenge.

Next, animal experiments were carried out to explore the potential combinatorial use of TLR ligands in vaccine development. Mice were immunized intrarectally with an HIV Env peptide as antigen together with various TLR ligands in a DOTAP liposome formulation. It was found that the combination of MALP-2 (a TLR2 ligand) and PolyI:C (a TLR3 ligand) synergistically induced mucosal memory CD8+ T cells that were specific for the given antigen (FIG. 13A). When immunized mice were challenged rectally with vaccinia virus expressing the vaccine antigen, use of these two ligands as adjuvant resulted in a reduction in viral replication at the mucosal site. However, in conjunction with CpG oligodeoxynucleotides (a TLR9 ligand), these ligands even more effectively induced antigen-specific memory CD8+ T cells (FIG. 13A) and enhanced the mucosal protection against virus challenge (FIG. 13B).

The synergistic TLR combinations described herein are associated with detection of both dsRNA and either bacterial surface molecules or genomic DNA by DCs. One possibility is that the host uses "a double key" system to distinguish danger signals from innocuous stimuli when endotoxins as TLR4 ligands are unseen or absent from some microbes. This might ensure an effective pathogen recognition and adaptive immunity against microbial invasion. Another possibility is that the host can instantaneously mount an immune response against an infection that may ensue. The "double key" design may avoid unnecessary activation of adaptive immunity if infection is unlikely to occur in the absence of dsRNA or only the presence of single ligands. This mechanism may be distinct from those used by macrophages and epithelial cells that respond to TLR ligands to mediate direct antimicrobial innate effector responses (45, 46).

It is possible that there still might be subtle differences in the combinatorial effects between TLR2+3 and TLR3+9 combination, although both ultimately lead to similar levels of T cell priming. The TLR2+3 is effective in inducing both IL-12-producing cells and IL-12 secretion, while the TLR3+9 combination seemed to preferentially increase numbers of IL-12-producing cells rather than produce a large quantity of the cytokine. Such divergence may imply a fine-tuning mechanism in response to different TLR ligands that may induce some different genes (47).

TLR2 recognizes its ligands by forming heterodimers with either TLR1 or 6 depending on whether the ligands are triacylated or diacylated, respectively (48-50). MALP-2 and LTA are diacylated lipoproteins, while PGN and PAM3CSK4 are triacylated. This difference in acylation might account for the differences in the level of DC activities observed between the two subgroups. PGN and PAM3CSK4 which act through TLR2/1 did not synergize with PolyI:C to upregulate IL-12 production, whereas MALP-2 and LTA which act through TLR2/6 did (FIG. 9A). PAM3CSK has been found not to favor IL-12 production (51). Thus, TLR2/6 and 2/1 might signal differently to more selectively determine priming or tolerance (51) (47), in combination with TLR3, which is mirrored by endotoxin-induced TLR4-mediated tolerance (52, 53).

The data presented herein shows that the immune system strategically utilizes TLRs involving at least two distinct signal transduction pathways, MyD88-dependent and -independent, to boost T cell responses, through synergistically amplifying DC functions in producing MyD88-dependent cytokines/chemokines. Stimulation through TLR3 along with either TLR 2 or 9 with their specific ligands, at suboptimal doses of each that were less effective individually, synergistically activated DCs and induced T cell responses. These doses may mimic the low levels found early in an infection, suggesting that the synergy may allow earlier detection of certain organisms. Concurrent triggering of TLR3 potentiated the MyD88 signaling pathway for TLR2 and 9, leading to amplification of MyD88-cJun dependent cytokines/chemokines such as IL-12 and TNF, while in contrast the MyD88-independent TLR3-mediated TRIF signaling pathway inducing DC maturation was not enhanced by TLR2 or 9 signaling through MyD88. Multiple MyD88-dependent cytokines were required for the synergy. Moreover, TLR2 and TLR9 did not synergize with each other in MyD88-dependent DC activation or in subsequent activation of T cells. Thus, the results presented herein demonstrate that the host utilizes TLRs strategically through at least two distinct signaling pathways in two-key design to sense microbial components and boost immune responses.

Example 6

Combinatorial Use of TLR Ligands in Vaccine Development

As reported herein, PolyI:C (for TLR3) can synergize with either MALP-2 (for TLR2) or CpG (for TLR9) in priming antigen-specific T cells through synergistic activation of dendritic cells. In a further series of experiments, the combinatorial use of the three ligands was next examined. It was found that an even more potent immune response was seen when the three types of ligands, PolyI:C, MALP-2 and CpG, were used together. Immunization with the triple ligands in a peptide vaccine for HIV provided an even greater protection against virus challenge compared to the double synergistic combination of TLR ligands, which was still effective.

Figure 14:
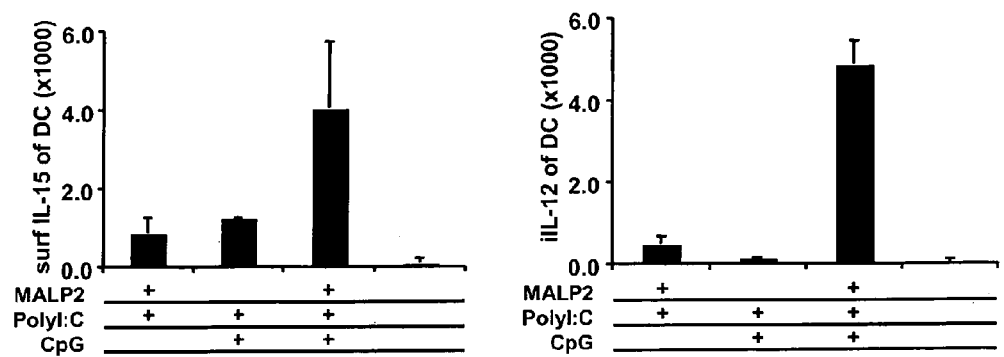
FIG. 14 is a graph that shows cytokine production by dendritic cells in draining lymph nodes after immunization.

FIG. 14 shows that the triple ligands are able to stimulate dendritic cells to produce a high level of IL-15, which can be detected on the cell surface. In FIG. 14, cytokine production by dendritic cells in draining lymph nodes after immunization is measured. BALB/c mice were treated with TLR ligands as indicated in the footpad. Two days later, the popliteal lymph nodes were removed and production of surface IL-15 (left) and IL-12 (right) by dendritic cells were analyzed.

Figure 15:
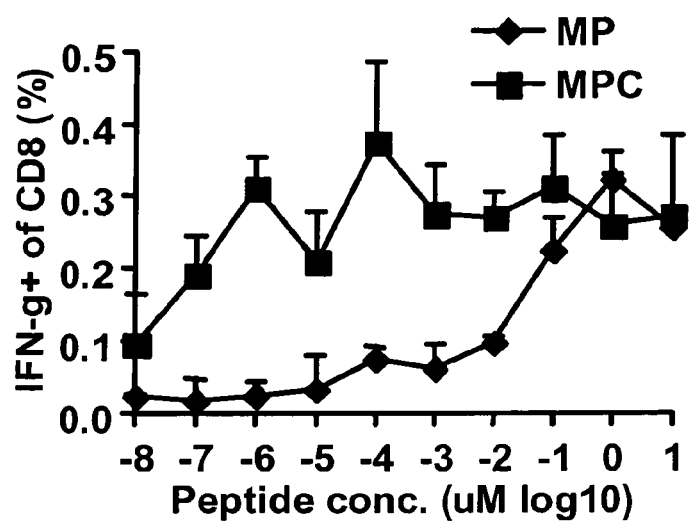
FIG. 15 is a graph that shows induction of high functional avidity T cells by the triple TLR ligands.

The triple TLR ligands may not increase the frequency but the quality of antigen-specific T cells compared to the double combinations. In a next set of experiments, mice were immunized with TLR ligands (MP: MALP-2+PolyI:C; MPC: MALP-2+PolyI:C+CpG) together with PCLUS3-18IIIB containing HIV CTL epitope. Five days later, popliteal lymph node cells were isolated and restimulated with P18I10 peptide as the CTL epitope stimulant at concentrations from high to low. Functional CD8+ T cells were assessed in 5 hours by intracellular staining of IFN-γ production. The results are shown in FIG. 15. Response at low concentration of peptide (such as 10-3 µM) is due to high avidity CTL whereas both high and low avidity CTL respond at 10 µM. Nearly all the CTL resulting from the triple TLR ligand combination (MPC) are high avidity, responding at both concentrations, whereas only about 20% of those induced by the double combination (MP) are high avidity. As shown in FIG. 15, these results show that immunization with the triple TLR ligands MALP-2+PolyI:C+CpG and a HIV vaccine peptide in the footpad primed more antigen-specific CD8+ T cells with high functional avidity in contrast to the double synergistic combination MALP-2 and PolyI:C.

The TLR-based defense mechanism described herein will have important implications for the development of both safe and effective vaccine strategies, avoiding the need for high-dose TLR ligands. The interplay of TLR3 with TLR2 or 9 as shown herein may represent an effective means of pathogen recognition, possibly as an alternative to TLR4, and appears to be advantageous especially when organisms lacking endotoxins (or other TLR4 ligands) are invading. In addition to providing important insight into the role of TLRs in pattern recognition and immune induction, the TLR interplay mechanism described here may be useful to develop safer (low dose), less expensive (compared to recombinant cytokines) but more effective vaccine strategies, without a need for endotoxin and avoiding potential side effects of high doses of single TLR ligands.

As the double combinations of PolyI:C and MALP-2 or CpG can activate dendritic cells in a synergistic way to raise immune responses by increasing antigen-specific T cell numbers, the triple combination of these ligands further boosts the immune responses by improving the quality of the T cells. Accordingly, effective control of virus challenge is attributed to the induction of specific T cells with high functionality.

Taken together, the results reported herein have elucidated the intracellular molecular mechanism that account for the synergistic immune response initiated within DCs in response to multiple TLR ligands. The novel unidirectional intracellular crosstalk between the TLR signaling pathways provides important insight into the host defense in response to combinatorial microbial components that alert the host to infection. Such an immune activation mechanism may lead to a new rationale in the design of more effective vaccines using multicomponent immune adjuvants, without the need for endotoxin or high doses of single TLR ligands.

Methods and Materials

The invention was performed using the following methods:

Animals and Reagents

Female BALB/c and C57BL/6 mice (6-8 weeks) were purchased from Frederick Cancer Research Center (Frederick, Md.) or Taconic (Hudson, N.Y.) and housed in pathogen-free conditions in the National Cancer Institute Animal Facility. MyD88−/−, bred at the FDA, were generated as previously described (54). All animal experiments were approved by the Animal Care and Use Committee of the National Cancer Institute.

PCLUS3-18IIIB (KQIINMWQEVGKAMYAPPISGQIR-RIQRGPGRAFVTIGK), P18-I10 (RGPGRAFVTI) and OVA257-264 (SIINFEKL) were synthesized by NeoMPS (San Diego, Calif.). Equimolar mixtures of the phosphorothioate CpG ODNs 1555 (GCTAGACGTTAGCGT) and 1466 (TCAACGTTGA) or control ODNs 1612 (GCTAGATGTTAGCGT) and 1471 (TCAAGCTTGA) were synthesized at the CBER core facility. All were free of endotoxin and protein contamination. Lipoteichoic acids (LTA), macrophage activating lipoprotein (MALP-2), zymosan (Zym), Pam3CSK4 (Pam3), polyinosine-polycytidylic acid (PolyI:C or PIC), lipopolysaccharide (LPS), monophosphoryl lipid A (MPL), and suppressive ODN 2088 were purchased from Invivogen (San Diego, Calif.). E6020 (a TLR4 ligand) were obtained from Eisai Corp. (Teaneck, N.J.). Dosage of MALP-2, PolyI:C and CpG ODN was otherwise indicated: 0.1, 20, 3 µg/ml in vitro or 0.1, 30, 5 µg in vivo based on induction of minimal amounts of IL-12 or CD86 expression. Inhibitors for P38, ERK, JNK and NF-kB were purchased from EMD Biosciences Inc. (San Diego, Calif.). Neutralizing antibodies for IL-12p70, IL-1b, IL-6, TNFa were purchased from R&D Systems Inc. or eBioscience (San Diego, Calif.). Recombinant IL-12, TNFa, MIP-1a and IP-10 proteins were purchased from Peprotech (Rocky Hill, N.J.).

Cell Isolation, Purification and Coculture

Bone marrow-derived dendritic cells (BMDCs) were generated as previously described (55). Bone marrow cells were cultured at 7'105/ml for 6 days in the presence of 15 ng/ml GM-CSF (Peprotech, Rocky Hill, N.J.) in RPMI 1640 medium supplemented with 10% heat-inactivated fetal calf serum, 2 mM L-glutamine, 100 U/ml penicillin, and 100 µg/ml streptomycin. DCs and macrophages were obtained from suspension and adherent cells, respectively (55).

Popliteal lymph node (LN) cells were isolated after footpad immunization either with DCs or with peptide. For T cell purification, spleens were removed from naïve mice. Total T cells as well as CD4+ and CD8+ T cell subsets were separated by negative separation (to avoid perturbation) on an autoMACS Separator (Miltenyi Biotec Inc., Auburn, Calif.) using a cocktail of antibodies against CD45R, CD49b, CD11b and Ter-119, and/or CD8a or CD4. The purity of sorted cell populations was at least 97%.

Besides BMDCs and macrophages, young adult mouse colon (YAMC) and mouse small intestine epithelial (MSIE) cells, kindly provided by Dr. Robert Whitehead (56), were used as stimulators. After 20 hours of stimulation with various TLR ligands, cells were washed to remove excess reagents. Purified total T or T subsets were used as responders, cocultured with stimulators at a ratio of 1:2.5.

Immunization

For subcutaneous immunization with peptide, peptide (20 µg of PCLUS3-18IIIB or 100 µg of SIINFEKL) and TLR ligands or recombinant cytokine proteins were mixed and given by footpad injection at day 0, 1 and 2. For immunization with DCs, 2×10⁵ of DCs were stimulated with TLR ligands in vitro for 20 hours and pulsed with peptide (5 μM of P18I10 or 20 μM of SIINFEKL) for 2 hours. At least three animals or samples were included in each group and time point of experiments.

Flow Cytometry and Cytokine Measurements

Antibodies for flow cytometry were purchased from eBioscience or BD Biosciences (San Jose, Calif.). To measure intracellular IFN-g in T cells, cells were stimulated for 5 hours at 37° C. with peptide P18I10 (10 nM) or SIINFEKL (100 nM) in the presence of 1 mg/ml of brefeldin A. To measure intracellular cytokine IL-12 in vitro cultured DCs, cells were stimulated with TLR ligands for 20 hours before staining of IL-12p70/40. LN cells isolated 36 hours after peptide immunization were assayed ex vivo for intracellular cytokines as previously described (57). Following surface staining, cells were fixed and permeabilized and then incubated with antibodies against cytokines. Sample data were acquired on a FACSCalibur or LSR II (BD, Sunnyvale, Calif.) and analyzed with FlowJo software (TreeStar Inc, Ashland, Oreg.).

To determine secreted cytokines and chemokines from DCs, culture supernatants were collected and measured with LINCOplex Kits (Linco Research Inc., St. Charles, Mo.) on a Bio-Plex System (Hercules, Calif.) using Luminex xMAP Technology or with MSD Multiplex Kits on a SECTOR Imager, an electrochemiluminescence multiplex system (Meso Scale Discovery, Gaithersburg, Md.) according to the manufacturer's instructions. Supernatants were incubated with capture antibodies for 2 hours at room temperature with shaking.

Statistical Analysis

Comparisons between groups were analyzed by Student's t-test. P values less than 0.05 were considered statistically significant. The pairwise correlation between DC functions and T cell activation was estimated by Pearson's correlation coefficient (r).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

CITATIONS

The following documents are cited herein. Many of the following documents are referred to above by a reference number as listed sequentially below within parentheses or brackets, e.g. (1).

1. Medzhitov, R., and C. A. Janeway, Jr. 1998. Innate immune recognition and control of adaptive immune responses. Semin Immunol 10:351-353.
2. Granucci, F., and P. Ricciardi-Castagnoli. 2003. Interactions of bacterial pathogens with dendritic cells during invasion of mucosal surfaces. Curr Opin Microbiol 6:72-76.
3. Akira, S., and K. Takeda. 2004. Toll-like receptor signalling. Nat Rev Immunol 4:499-511.
4. Blander, J. M., and R. Medzhitov. 2006. Toll-dependent selection of microbial antigens for presentation by dendritic cells. Nature 440:808-812.
5. Schuster, J. M., and P. S. Nelson. 2000. Toll receptors: an expanding role in our understanding of human disease. J Leukoc Biol 67:767-773.
6. Zarember, K. A., and P. J. Godowski. 2002. Tissue expression of human Toll-like receptors and differential regulation of Toll-like receptor mRNAs in leukocytes in response to microbes, their products, and cytokines. J Immunol 168:554-561.
7. Abreu, M. T., M. Fukata, and M. Arditi. 2005. TLR signaling in the gut in health and disease. J Immunol 174:4453-4460.
8. Kabelitz, D. 2007. Expression and function of Toll-like receptors in T lymphocytes. Curr Opin Immunol 19:39-45.
9. Takeda, K., T. Kaisho, and S. Akira. 2003. Toll-like receptors. Annu Rev Immunol 21:335-376.
10. Yamamoto, M., S. Sato, H. Hemmi, K. Hoshino, T. Kaisho, H. Sanjo, O. Takeuchi, M. Sugiyama, M. Okabe, K. Takeda, and S. Akira. 2003. Role of adaptor TRIF in the MyD88-independent toll-like receptor signaling pathway. Science 301:640-643.
11. Aliprantis, A. O., R. B. Yang, M. R. Mark, S. Suggett, B. Devaux, J. D. Radolf, G. R. Klimpel, P. Godowski, and A. Zychlinsky. 1999. Cell activation and apoptosis by bacterial lipoproteins through toll-like receptor-2. Science 285:736-739.
12. Brightbill, H. D., D. H. Libraty, S. R. Krutzik, R. B. Yang, J. T. Belisle, J. R. Bleharski, M. Maitland, M. V. Norgard, S. E. Plevy, S. T. Smale, P. J. Brennan, B. R. Bloom, P. J. Godowski, and R. L. Modlin. 1999. Host defense mechanisms triggered by microbial lipoproteins through toll-like receptors. Science 285:732-736.
13. Schwandner, R., R. Dziarski, H. Wesche, M. Rothe, and C. J. Kirschning. 1999. Peptidoglycan- and lipoteichoic acid-induced cell activation is mediated by toll-like receptor 2. J Biol Chem 274:17406-17409.
14. Poltorak, A., X. He, I. Smirnova, M. Y. Liu, C. Van Huffel, X. Du, D. Birdwell, E. Alejos, M. Silva, C. Galanos, M. Freudenberg, P. Ricciardi-Castagnoli, B. Layton, and B. Beutler. 1998. Defective LPS signaling in C3H/HeJ and C57BL/10ScCr mice: mutations in Tlr4 gene. Science 282:2085-2088.
15. Hayashi, F., K. D. Smith, A. Ozinsky, T. R. Hawn, E. C. Yi, D. R. Goodlett, J. K. Eng, S. Akira, D. M. Underhill, and A. Aderem. 2001. The innate immune response to bacterial flagellin is mediated by Toll-like receptor 5. Nature 410:1099-1103.
16. Yarovinsky, F., D. Zhang, J. F. Andersen, G. L. Bannenberg, C. N. Serhan, M. S. Hayden, S. Hieny, F. S. Sutterwala, R. A. Flavell, S. Ghosh, and A. Sher. 2005. TLR11 activation of dendritic cells by a protozoan profilin-like protein. Science 308:1626-1629.
17. Hemmi, H., O. Takeuchi, T. Kawai, T. Kaisho, S. Sato, H. Sanjo, M. Matsumoto, K. Hoshino, H. Wagner, K. Takeda, and S. Akira. 2000. A Toll-like receptor recognizes bacterial DNA. Nature 408:740-745.
18. Heil, F., H. Hemmi, H. Hochrein, F. Ampenberger, C. Kirschning, S. Akira, G. Lipford, H. Wagner, and S. Bauer.

2004. Species-specific recognition of single-stranded RNA via toll-like receptor 7 and 8. Science 303:1526-1529.

19. Diebold, S. S., T. Kaisho, H. Hemmi, S. Akira, and C. Reis e Sousa. 2004. Innate antiviral responses by means of TLR7-mediated recognition of single-stranded RNA. Science 303:1529-1531.

20. Lund, J. M., L. Alexopoulou, A. Sato, M. Karow, N. C. Adams, N. W. Gale, A. Iwasaki, and R. A. Flavell. 2004. Recognition of single-stranded RNA viruses by Toll-like receptor 7. Proc Natl Acad Sci USA 101:5598-5603.

21. Alexopoulou, L., A. C. Holt, R. Medzhitov, and R. A. Flavell. 2001. Recognition of double-stranded RNA and activation of NF-kappaB by Toll-like receptor 3. Nature 413:732-738.

22. Beutler, B., Z. Jiang, P. Georgel, K. Crozat, B. Croker, S. Rutschmann, X. Du, and K. Hoebe. 2006. Genetic analysis of host resistance: Toll-like receptor signaling and immunity at large. Annu Rev Immunol 24:353-389.

23. Chang, L., and M. Karin. 2001. Mammalian MAP kinase signalling cascades. Nature 410:37-40.

24. Dong, C., R. J. Davis, and R. A. Flavell. 2002. MAP kinases in the immune response. Annu Rev Immunol 20:55-72.

25. Hoebe, K., E. M. Janssen, S. O. Kim, L. Alexopoulou, R. A. Flavell, J. Han, and B. Beutler. 2003. Upregulation of costimulatory molecules induced by lipopolysaccharide and double-stranded RNA occurs by Trif-dependent and Trif-independent pathways. Nat Immunol 4:1223-1229.

26. Napolitani, G., A. Rinaldi, F. Bertoni, F. Sallusto, and A. Lanzavecchia. 2005. Selected Toll-like receptor agonist combinations synergistically trigger a T helper type 1-polarizing program in dendritic cells. Nat Immunol 6:769-776.

27. Trinchieri, G., and A. Sher. 2007. Cooperation of Toll-like receptor signals in innate immune defence. Nat Rev Immunol 7:179-190.

28. Gautier, G., M. Humbert, F. Deauvieau, M. Scuiller, J. Hiscott, E. E. Bates, G. Trinchieri, C. Caux, and P. Garrone. 2005. A type I interferon autocrine-paracrine loop is involved in Toll-like receptor-induced interleukin-12p70 secretion by dendritic cells. J Exp Med 201:1435-1446.

29. Warger, T., P. Osterloh, G. Rechtsteiner, M. Fassbender, V. Heib, B. Schmid, E. Schmitt, H. Schild, and M. P. Radsak. 2006. Synergistic activation of dendritic cells by combined Toll-like receptor ligation induces superior CTL responses in vivo. Blood 108:544-550.

30. Roelofs, M. F., L. A. Joosten, S. Abdollahi-Roodsaz, A. W. van Lieshout, T. Sprong, F. H. van den Hoogen, W. B. van den Berg, and T. R. Radstake. 2005. The expression of toll-like receptors 3 and 7 in rheumatoid arthritis synovium is increased and costimulation of toll-like receptors 3, 4, and 7/8 results in synergistic cytokine production by dendritic cells. Arthritis Rheum 52:2313-2322.

31. Sato, S., F. Nomura, T. Kawai, O. Takeuchi, P. F. Muhlradt, K. Takeda, and S. Akira. 2000. Synergy and cross-tolerance between toll-like receptor (TLR) 2- and TLR4-mediated signaling pathways. J Immunol 165:7096-7101.

32. Faure, E., L. Thomas, H. Xu, A. Medvedev, O. Equils, and M. Arditi. 2001. Bacterial lipopolysaccharide and IFN-gamma induce Toll-like receptor 2 and Toll-like receptor 4 expression in human endothelial cells: role of NF-kappa B activation. J Immunol 166:2018-2024.

33. Liang, M. D., A. Bagchi, H. S. Warren, M. M. Tehan, J. A. Trigilio, L. K. Beasley-Topliffe, B. L. Tesini, J. C. Lazzaroni, M. J. Fenton, and J. Hellman. 2005. Bacterial peptidoglycan-associated lipoprotein: a naturally occurring toll-like receptor 2 agonist that is shed into serum and has synergy with lipopolysaccharide. J Infect Dis 191:939-948.

34. Ahlers, J. D., C. D. Pendleton, N. Dunlop, A. Minassian, P. L. Nara, and J. A. Berzofsky. 1993. Construction of an HIV-1 peptide vaccine containing a multideterminant helper peptide linked to a V3 loop peptide 18 inducing strong neutralizing antibody responses in mice of multiple MHC haplotypes after two immunizations. J Immunol 150:5647-5665.

35. Yamamoto, M., S. Sato, H. Hemmi, S. Uematsu, K. Hoshino, T. Kaisho, O. Takeuchi, K. Takeda, and S. Akira. 2003. TRAM is specifically involved in the Toll-like receptor 4-mediated MyD88-independent signaling pathway. Nat Immunol 4:1144-1150.

36. Hirotani, T., M. Yamamoto, Y. Kumagai, S. Uematsu, I. Kawase, O. Takeuchi, and S. Akira. 2005. Regulation of lipopolysaccharide-inducible genes by MyD88 and Toll/IL-1 domain containing adaptor inducing IFN-beta. Biochem Biophys Res Commun 328:383-392.

37. Schmidt, C. S., and M. F. Mescher. 2002. Peptide antigen priming of naive, but not memory, CD8 T cells requires a third signal that can be provided by IL-12. J Immunol 168:5521-5529.

38. Curtsinger, J. M., D. C. Lins, and M. F. Mescher. 2003. Signal 3 determines tolerance versus full activation of naive CD8 T cells: dissociating proliferation and development of effector function. J Exp Med 197:1141-1151.

39. Lenschow, D. J., T. L. Walunas, and J. A. Bluestone. 1996. CD28/B7 system of T cell costimulation. Annu Rev Immunol 14:233-258.

40. Albert, M. L., M. Jegathesan, and R. B. Darnell. 2001. Dendritic cell maturation is required for the cross-tolerization of CD8+ T cells. Nat Immunol 2:1010-1017.

41. Chu, W. M., D. Ostertag, Z. W. Li, L. Chang, Y. Chen, Y. Hu, B. Williams, J. Perrault, and M. Karin. 1999. JNK2 and IKKbeta are required for activating the innate response to viral infection. Immunity 11:721-731.

42. Park, C., S. Lee, I. H. Cho, H. K. Lee, D. Kim, S. Y. Choi, S. B. Oh, K. Park, J. S. Kim, and S. J. Lee. 2006. TLR3-mediated signal induces proinflammatory cytokine and chemokine gene expression in astrocytes: differential signaling mechanisms of TLR3-induced IP-10 and IL-8 gene expression. Glia 53:248-256.

43. Kawai, T., O. Adachi, T. Ogawa, K. Takeda, and S. Akira. 1999. Unresponsiveness of MyD88-deficient mice to endotoxin. Immunity 11:115-122.

44. Kaisho, T., O. Takeuchi, T. Kawai, K. Hoshino, and S. Akira. 2001. Endotoxin-induced maturation of MyD88-deficient dendritic cells. J Immunol 166:5688-5694.

45. Thoma-Uszynski, S., S. Stenger, O. Takeuchi, M. T. Ochoa, M. Engele, P. A. Sieling, P. F. Barnes, M. Rollinghoff, P. L. Bolcskei, M. Wagner, S. Akira, M. V. Norgard, J. T. Belisle, P. J. Godowski, B. R. Bloom, and R. L. Modlin. 2001. Induction of direct antimicrobial activity through mammalian toll-like receptors. Science 291:1544-1547.

46. Hertz, C. J., Q. Wu, E. M. Porter, Y. J. Zhang, K. H. Weismuller, P. J. Godowski, T. Ganz, S. H. Randell, and R. L. Modlin. 2003. Activation of Toll-like receptor 2 on human tracheobronchial epithelial cells induces the antimicrobial peptide human beta defensin-2. J Immunol 171:6820-6826.

47. Pulendran, B. 2005. Variegation of the immune response with dendritic cells and pathogen recognition receptors. J Immunol 174:2457-2465.

48. Ozinsky, A., D. M. Underhill, J. D. Fontenot, A. M. Hajjar, K. D. Smith, C. B. Wilson, L. Schroeder, and A. Aderem.

2000. The repertoire for pattern recognition of pathogens by the innate immune system is defined by cooperation between toll-like receptors. Proc Natl Acad Sci USA 97:13766-13771.
49. Takeuchi, O., T. Kawai, P. F. Muhlradt, M. Morr, J. D. Radolf, A. Zychlinsky, K. Takeda, and S. Akira 2001. Discrimination of bacterial lipoproteins by Toll-like receptor 6. Int Immunol 13:933-940.
50. Takeuchi, O., S. Sato, T. Horiuchi, K. Hoshino, K. Takeda, Z. Dong, R. L. Modlin, and S. Akira. 2002. Cutting edge: role of Toll-like receptor 1 in mediating immune response to microbial lipoproteins. J Immunol 169:10-14.
51. Agrawal, S., A. Agrawal, B. Doughty, A. Gerwitz, J. Blenis, T. Van Dyke, and B. Pulendran. 2003. Cutting edge: different Toll-like receptor agonists instruct dendritic cells to induce distinct Th responses via differential modulation of extracellular signal-regulated kinase-mitogen-activated protein kinase and c-Fos. J Immunol 171:4984-4989.
52. Fan, H., and J. A. Cook. 2004. Molecular mechanisms of endotoxin tolerance. J Endotoxin Res 10:71-84.
53. Fujihara, M., M. Muroi, K. Tanamoto, T. Suzuki, H. Azuma, and H. Ikeda. 2003. Molecular mechanisms of macrophage activation and deactivation by lipopolysaccharide: roles of the receptor complex. Pharmacol Ther 100:171-194.
54. Adachi, O., T. Kawai, K. Takeda, M. Matsumoto, H. Tsutsui, M. Sakagami, K. Nakanishi, and S. Akira. 1998. Targeted disruption of the MyD88 gene results in loss of IL-1- and IL-18-mediated function. Immunity 9:143-150.
55. Lutz, M. B., N. Kukutsch, A. L. Ogilvie, S. Rossner, F. Koch, N. Romani, and G. Schuler. 1999. An advanced culture method for generating large quantities of highly pure dendritic cells from mouse bone marrow. J Immunol Methods 223:77-92.
56. Whitehead, R. H., P. E. VanEeden, M. D. Noble, P. Ataliotis, and P. S. Jat. 1993. Establishment of conditionally immortalized epithelial cell lines from both colon and small intestine of adult H-2Kb-tsA58 transgenic mice. Proc Natl Acad Sci USA 90:587-591.
57. Belyakov, I. M., D. Isakov, Q. Zhu, A. Dzutsev, and J. A. Berzofsky. 2007. A Novel Functional CTL Avidity/Activity Compartmentalization to the Site of Mucosal Immunization Contributes to Protection of Macaques against Simian/Human Immunodeficiency Viral Depletion of Mucosal CD4+ T Cells. J Immunol 178:7211-7221.

What is claimed is:

1. An immunostimulatory composition for inducing high functional avidity T cells comprising a combination of three or more Toll Like Receptor (TLR) agonists, said composition comprising an effective amount of MALP-2, a TLR2 agonist, polyI:C, a TLR3 agonist, and CpG, a TLR9 agonist, wherein the triple combination of TLR agonists synergistically activates IL-15 and IL-12 production of dendritic cells as compared to a double combination of TLR agonists thereby inducing high functional avidity T cells.

2. The immunostimulatory composition of claim 1 further comprising one or more antigens.

3. The immunostimulatory composition of claim 2 wherein the antigen is conjugated to a TLR agonist.

4. An immunostimulatory composition according to claim 1 that is effective for inducing an immune response to the antigen in a subject immunized with the immunostimulatory composition.

5. The immunostimulatory composition according to claim 1 wherein the antigen comprises a tumor antigen, a viral antigen, a bacterial antigen, a fungal antigen, a parasitic antigen, an alloantigen, or a xenoantigen.

6. A method of activating dendritic cells (DCs) to form high functional avidity T cells in a subject comprising administering to the subject an effective amount of a immunostimulatory composition comprising a combination of three or more Toll Like Receptor (TLR) agonists, said composition comprising an effective amount of MALP-2, a TLR2 agonist, polyI:C, a TLR3 agonist, and CpG, a TLR9 agonist, wherein the triple combination of TLR agonists synergistically activates IL-15 and IL-12 production of the dendritic cells as compared to a double combination of TLR agonists thereby inducing high functional avidity T cells.

7. The method of activating dendritic cells (DCs) in a subject of claim 6 wherein each TLR agonist alone induces limited or no immune response.

8. The method of activating dendritic cells (DCs) in a subject of claim 6 further comprising co-administering one or more antigens.

9. A method of activating antigen-specific CD8+ T cells in a subject comprising administering to the subject an effective amount of the immunostimulatory composition of claim 1.

10. A pharmaceutical composition for inducing high functional avidity T cells comprising a combination of three or more Toll Like Receptor (TLR) agonists, said composition comprising an effective amount of MALP-2, a TLR2 agonist, polyI:C, a TLR3 agonist, and CpG, a TLR9 agonist, wherein the triple combination of TLR agonists synergistically activates IL-15 and IL-12 production of dendritic cells as compared to a double combination of TLR agonists thereby inducing high functional avidity T cells.

* * * * *